(12) United States Patent
Pajouhesh et al.

(10) Patent No.: US 7,649,092 B2
(45) Date of Patent: Jan. 19, 2010

(54) UREA DERIVATIVES AS CALCIUM CHANNEL BLOCKERS

(75) Inventors: Hassan Pajouhesh, West Vancouver (CA); Hossein Pajouhesh, Coquitlam (CA); Yanbing Ding, Richmond (CA); Terrance P. Snutch, Vancouver (CA)

(73) Assignee: Neuromed Pharmaceuticals Ltd., Vancouver (CA)

( * ) Notice: Subject to any disclaimer, the term of this patent is extended or adjusted under 35 U.S.C. 154(b) by 0 days.

(21) Appl. No.: 12/111,131

(22) Filed: Apr. 28, 2008

(65) Prior Publication Data

US 2008/0207633 A1 Aug. 28, 2008

Related U.S. Application Data

(62) Division of application No. 11/215,064, filed on Aug. 30, 2005, now Pat. No. 7,378,420.

(60) Provisional application No. 60/605,615, filed on Aug. 30, 2004.

(51) Int. Cl.
C07D 241/04 (2006.01)
C07D 295/00 (2006.01)
(52) U.S. Cl. .................................................. 544/358
(58) Field of Classification Search .................. None
See application file for complete search history.

(56) References Cited

U.S. PATENT DOCUMENTS

| | | | |
|---|---|---|---|
| 5,428,038 A | 6/1995 | Chatterjee et al. | |
| 5,646,149 A | 7/1997 | Hellberg et al. | |
| 5,703,071 A | 12/1997 | Itoh et al. | |
| 6,011,035 A | 1/2000 | Snutch et al. | |
| 6,294,533 B1 | 9/2001 | Snutch et al. | |
| 6,310,059 B1 | 10/2001 | Snutch | |
| 6,458,781 B1 | 10/2002 | Connor et al. | |
| 6,492,375 B2 | 12/2002 | Snutch | |
| 6,943,168 B2 | 9/2005 | Snutch et al. | |
| 6,949,554 B2 | 9/2005 | Snutch et al. | |
| 6,951,862 B2 | 10/2005 | Snutch et al. | |
| 2002/0019389 A1 | 2/2002 | Kim | |
| 2004/0034035 A1 | 2/2004 | Snutch et al. | |
| 2004/0044004 A1 | 3/2004 | Snutch et al. | |
| 2004/0147529 A1 | 7/2004 | Snutch et al. | |
| 2004/0192703 A1 | 9/2004 | Snutch et al. | |
| 2004/0259866 A1 | 12/2004 | Snutch et al. | |
| 2004/0266784 A1 | 12/2004 | Snutch et al. | |
| 2006/0084660 A1 | 4/2006 | Snutch et al. | |

FOREIGN PATENT DOCUMENTS

| | | |
|---|---|---|
| CA | 2 335 461 | 1/2000 |
| EP | 0 441 226 | 8/1991 |
| WO | WO-97/24325 | 7/1997 |
| WO | WO-00/01375 | 1/2000 |
| WO | WO-01/45709 | 6/2001 |
| WO | WO-01/46166 | 6/2001 |
| WO | WO-01/49670 | 7/2001 |
| WO | WO-01/85856 | 12/2001 |
| WO | WO-01/95856 | 12/2001 |
| WO | WO-2004/089377 | 10/2004 |
| WO | WO-2004/089922 | 10/2004 |

OTHER PUBLICATIONS

Gribkopf et al. Expert Opinion in Investigational Drugs, 2005, 14(5), 579-592.*
"Ameliorate", http://www.merriam-webster.com/dictionary/ameliorate, accessed Dec. 8, 2008.*
"Mood disorders", http://www.nlm.nih.gov/cgi/mesh/2008/MB_cgi, accessed Dec. 8, 2008.*
"Neurodegenerative Diseases", http://www.nlm.nih.gov/cgi/mesh/2008/MB_cgi, accessed Dec. 8, 2008.*
"Gastrointestinal diseases", http://www.nlm.nih.gov/cgi/mesh/2008/MB_cgi?mode=&index=5541&field=all&HM=&II=&PA=&form=&input=, accessed Dec. 8, 2008.*
"Male Urogenital diseases", http://www.nlm.nih.gov/cgi/mesh/2008/MB_cgi?mode=&index=23886&field=all&HM=&II=&PA=& form=&input=, accessed Dec. 8, 2008.*
"Female Urogenital Diseases", http://www.nlm.nih.gov/cgi/mesh/2008/MB_cgi?mode=&index=23878&field=all&HM=&II=&PA=& form=&input=, accessed Dec. 8, 2008.*
"Metabolic Diseases", http://www.nlm.nih.gov/cgi/mesh/2008/MB_cgi, accessed Dec. 8, 2008.*
"Cardiovascular Diseases", http://www.nlm.nih.gov/cgi/mesh/2008/MB_cgi, accessed Dec. 8, 2008.*
"Sleep Disorders", http://www.nlm.nih.gov/cgi/mesh/2008/MB_cgi?mode=&index=12386&field=all&HM=&II=&PA=& form=&input=, Accessed Dec. 8, 2008.*
Collins et al. Expert Opinion on Emerging Drugs, 2005, 10(1), 95-108.*
Kwan et al. Expert Opinion on Emerging Drugs, 2007, 12(3), 407-22.*
Mariot et al. The Journal of Biological Chemistry, 2002, 277(13), 10284-10833.*
"Patient Care", http://rehab.washington.edu/patientcare/patientinfo/articles/sci_healthy.asp, accessed May 26, 2009.*
"Epilepsy-Prevention", http://www.webmd.com/epilepsy/tc/epilepsy-prevention, Accessed 26 May 29, 2009.*
"Future Prostate Cancer Treatments", http://www.webmd.com/prostate-cancer/guide/future-prostate-cancer-treatments, accessed May 26, 2009.*
"Type 1 Diabetes Prevention", http://diabetes.webmd.com/tc/type-1-diabetes-prevention, accessed May 26, 2009.*
"NDEP", http://ndep.nih.gov/diabetes/prev/prevention.htm, accessed May 26, 2009.*
"Epilepsy", http://www.nlm.nih.gov/cgi/mesh/2009/MB_cgi, accessed May 26, 2009.*

(Continued)

*Primary Examiner*—James O Wilson
*Assistant Examiner*—Noble Jarrell
(74) *Attorney, Agent, or Firm*—Morrison & Foerster LLP

(57) ABSTRACT

Urea derivatives which comprise piperidine or piperazine rings and further substitution are effective in ameliorating conditions characterized by unwanted calcium ion channel activity.

8 Claims, No Drawings

OTHER PUBLICATIONS

"Epilepsy, Generalized", http://www.nlm.nih.gov/cgi/mesh/2009/MB_cgi?mode=&term=Epilepsy,+Generalized&field=entry, accessed May 26, 2009.*

"Epilepsies, myoclonic", http://www.nlm.nih.gov/cgi/mesh/2009/MB_cgi?mode=&term=Epilepsies,+Myoclonic&field=entry, accessed May 26, 2009.*

"Epilepsies, Post-Traumatic", http://www.nlm.nih.gov/cgi/mesh/2009/MB_cgi?mode=&term=Epilepsy,+Post-Traumatic&field=entry, accessed May 26, 2009.*

"Epilepsy, Reflex", http://www.nlm.nih.gov/cgi/mesh/2009/MB_cgi?mode=&term=Epilepsy,+Reflex&field=entry, accessed May 26, 2009.*

"Status Epilepticus", http://www.nlm.nih.gov/cgi/mesh/2009/MB_cgi?mode=&term=Status+Epilepticus&field=entry, accessed May 26, 2009.*

"Seizures, Febrile", http://www.nlm.nih.gov/cgi/mesh/2009/MB_cgi?mode=&term=Seizures,+Febrile&field=entry, accessed May 26, 2009.*

"Diabetes Insipidus", http://www.nlm.nih.gov/cgi/mesh/2009/MB_cgi?mode=&index=3759&field=all&HM=&II=&PA=&form=&input=, accessed May 26, 2009.*

"Diabetes, Insipidus, Nephrogenic", http://www.nlm.nih.gov/cgi/mesh/2009/MB_cgi?mode=&term=Diabetes+Insipidus,+Nephrogenic&field=entry, accessed May 26, 2009.*

"Diabetes Insipidus, Neurogenic", http://www.nlm.nih.gov/cgi/mesh/2009/MB_cgi?mode=&term=Diabetes+Insipidus,+Neurogenic&field=entry, accessed May 26, 2009.*

"Diabetes Mellitus", http://www.nlm.nih.gov/cgi/mesh/2009/MB_cgi?mode=&term=Diabetes+Mellitus&field=entry, accessed May 26, 2009.*

"Diabetes Mellitus, Experimental", http://www.nlm.nih.gov/cgi/mesh/2009/MB_cgi?mode=&term=Diabetes+Mellitus,+Experimental&field=entry, accessed May 26, 2009.*

"Diabetes, Gestational", http://www.nlm.nih.gov/cgi/mesh/2009/MB_cgi?mode=&term=Diabetes,+Gestational&field=entry, accessed May 26, 2009.*

"Diabetes Mellitus, Lipoatrophic", http://www.nlm.nih.gov/cgi/mesh/2009/MB_cgi?mode=&index=3763&field=all&HM=&II=&PA=&form=&input=, accessed May 26, 2009.*

"Diabetes Mellitus, Type 1", http://www.nlm.nih.gov/cgi/mesh/2009/MB_cgi?mode=&term=Diabetes+Mellitus,+Type+1&field=entry, accessed May 26, 2009.*

"Diabetes Mellitus, Type 2", http://www.nlm.nih.gov/cgi/mesh/2009/MB_cgi?mode=&term=Diabetes+Mellitus,+Type+2&field=entry, accessed May 26, 2009.*

Augustine et al., Annu. Rev. Neurosci. (1987) 10:633-693.
Backonja et al., JAMA (1998) 280:1831-1836.
Bowersox et al., J. Pharmacol. Exp. Ther. (1996) 279:1243-1249.
Caraceni et al., J. Pain & Symp. Manag. (1999) 17:441-445.
Catterall, Annu. Rev. Cell Dev. Biol. (2000) 16:521-555.
Cesena, Neuro. Sci. Lett. (1999) 262:101-104.
Cheng et al., Anesthesiology (2000) 92:1126-1131.
Di Trapani et al., Clin. Ter. (2000) 151:145-148.
Dogrul et al., Pain (2003) 105:159-168.
Dooley, Current Opinion in CPNS Investigational Drugs (1999) 1:116-125.
Field et al., Pain (1999) 80:391-398.
Gomora et al., Mol. Pharmacol. (2001) 60:1121-1132.
Gould et al., PNAS USA (1983) 80:5122-5125.
Grantham et al., Brit. J. Pharmacol. (1944) 111:483-488.
Hatakeyama et al., Neuro Report (2001) 12:2423-2427.
Heading, Curr. Opin. CPNS Investigational Drugs (1999) 1:153-166.
Heady et al., Jpn. J. Pharmacol. (2001) 85:339-350.
Houtchens et al., Multiple Sclerosis (1997) 3:250-253.
Huguenard, Annu. Rev. Physiol. (1996) 58:329-348.
Ino et al., PNAS USA (2001) 98:5323-5328.
International Search Report for PCT/CA2005/001324, mailed on Dec. 14, 2005, 6 pages.
Kim et al., Mol. Cell Neurosci. (2001) 18:235-245.
Kim et al., Neuron (2001) 31:35-45.
King et al., J. Biol. Chem. (1989) 264:5633-5641.
Laird et al., Annal. Pharmacotherap. (2000) 34:802-807.
Lavoie and Patani, Chemical Reviews (1996) 96:3147-3176.
Magnus, Epilepsia (1999) 40:S66-S72.
Malmberg et al., J. Neurosci. (1994) 14:4882-4890.
Mathur, Seminars in Anesthesia, Perioperative Medicine and Pain (2000) 19:67-75.
Miller, Science (1987) 235:46-52.
Nicholson, Acta. Neurol. Scand. (2000) 101:359-371.
Ridgeway et al., Pain (2000) 85:287-289.
Rowbotham et al., JAMA (1998) 280:1837-1842.
Saegusa et al., PNAS USA (2001) 97:6132-6137.
Sluka, J. Pharmacol. Exp. Ther. (1998) 287:232-237.
Stea et al., Handbook on Ion Channels, R.A. North (ed.), CRC Press, (1994) pp. 113-151.
Stea et al., PNAS USA (1994) 91:10576-10580.
Su et al., J. Neurosci. (2002) 22:3645-3655.
Taylor et al., Epilepsy Res. (1998) 29:233-249.
Vanegas et al., Pain (2000) 85:9-18.
Wang et al., Soc. Neurosci. Abstr. (1998) 24:1626.
March, Advanced Organic Chemistry, 1992, pp. 352-357 and 649-651.
MeSH, retrieved online at <http://www.ncbi.nlm.nih.gov/sites/entrez?Db=mesh&Cm...ystem2.PEntrez.Mesh.Mesh_ResultsPanel.Mesh_RVDocSum>, accessed Nov. 12, 2008.
Non-Final Office Action for U.S. Appl. No. 12/116,920, mailed on Nov. 26, 2008, 9 pages.
Carceller et al., J Med Chem (1992) 35:4118-4134.
Dutta et al., Journal of Medicinal Chemistry (2001) 44(6):937-948.
Final Office Action for U.S. Appl. No. 12/116,920, mailed on Jun. 11, 2009, 6 pages.
Supplementary European Search Report for EP 05782685.1, mailed Jun. 17, 2009, 5 pages.
Tsien et al., Annual Review of Biophysics and Bioengineering (1987) 16:265-290.

* cited by examiner

UREA DERIVATIVES AS CALCIUM CHANNEL BLOCKERS

CROSS-REFERENCE TO RELATED APPLICATION

This application is a divisional of U.S. application Ser. No. 11/215,064 filed 30 Aug. 2005, now allowed, which claims priority from U.S. provisional Patent Application No. 60/605,615 filed 30 Aug. 2004. The contents of these applications are incorporated herein by reference.

TECHNICAL FIELD

The invention relates to compounds useful in treating conditions associated with calcium channel function. More specifically, the invention concerns compounds containing substituted or unsubstituted urea-containing derivatives of 6-membered heterocyclic moieties that are useful in treatment of conditions such as stroke and pain.

BACKGROUND ART

The entry of calcium into cells through voltage-gated calcium channels mediates a wide variety of cellular and physiological responses, including excitation-contraction coupling, hormone secretion and gene expression (Miller, R. J., *Science* (1987) 235:46-52; Augustine, G. J., et al., *Annu Rev Neurosci* (1987) 10:633-693). In neurons, calcium channels directly affect membrane potential and contribute to electrical properties such as excitability, repetitive firing patterns and pacemaker activity. Calcium entry further affects neuronal functions by directly regulating calcium-dependent ion channels and modulating the activity of calcium-dependent enzymes such as protein kinase C and calmodulin-dependent protein kinase II. An increase in calcium concentration at the presynaptic nerve terminal triggers the release of neurotransmitter and calcium channels, which also affects neurite outgrowth and growth cone migration in developing neurons.

Calcium channels mediate a variety of normal physiological functions, and are also implicated in a number of human disorders. Examples of calcium-mediated human disorders include but are not limited to congenital migraine, cerebellar ataxia, angina, epilepsy, hypertension, ischemia, and some arrhythmias. The clinical treatment of some of these disorders has been aided by the development of therapeutic calcium channel antagonists (e.g., dihydropyridines, phenylalkyl amines, and benzothiazepines all target L-type calcium channels) (Janis, R. J., et al., *In Calcium Channels: Their Properties, Functions, Regulation and Clinical Relevance*, CRC Press, London, (1991).

Native calcium channels have been classified by their electrophysiological and pharmacological properties into T-, L-, N-, P/Q- and R-types (reviewed in Catterall, W., *Annu Rev Cell Dev Biol* (2000) 16:521-555; Huguenard (1996)). T-type (or low voltage-activated) channels describe a broad class of molecules that transiently activate at negative potentials and are highly sensitive to changes in resting potential.

The L-, N- and P/Q-type channels activate at more positive potentials (high voltage-activated) and display diverse kinetics and voltage-dependent properties (Catterall, supra; Huguenard, J. R., *Annu Rev Physiol* (1996) 58:329-348). L-type channels can be distinguished by their sensitivity to several classes of small organic molecules used therapeutically, including dihydropyridines (DHP's), phenylalkylamines and benzothiazepines. In contrast, N-type and P/Q-type channels are high affinity targets for certain peptide toxins produced by venous spiders and marine snails: N-type channels are blocked by the ω-conopeptides ω-conotoxin GVIA (ω-CTx-GVIA) isolated from *Conus geographus* and ω-conotoxin MVIIA (ω-CTx-MVIIA) isolated from *Conus magus*, while P/Q-type channels are resistant to ω-CTx-MVIIA but are sensitive to the funnel web spider peptide, ω-agatoxin IVA (ω-Aga-IVA). R-type calcium channels are sensitive to block by the tarantula toxin, SNX-482.

Neuronal high voltage-activated calcium channels are composed of a large (>200 kDa) pore-forming $\alpha_1$ subunit that is the target of identified pharmacological agents, a cytoplasmically localized ~50-70 kDa $\beta$ subunit that tightly binds the $\alpha_1$ subunit and modulates channel biophysical properties, and an ~170 kDa $\alpha_2\delta$ subunit (reviewed by Stea, A., et al. *Handbook on Ion Channels*, R. A. North (ed), CRC Press, (1994) 113-151; Stea, A., et al., *Proc. Natl. Acad. Sci. USA* (1994) 91:10576-10580; Catterall, supra). At the molecular level, nine different $\alpha_1$ subunit genes expressed in the nervous system have been identified and shown to encode all of the major classes of native calcium currents (Table 1).

TABLE 1

Classification of Neuronal Calcium Channels

| Native Class | cDNA | Gene Name | ω-AGA IVA | ω-CTx GVIA | ω-CTx MVIA | dihydro-pyridines |
|---|---|---|---|---|---|---|
| P/Q-type | $\alpha_{1A}$ | $Ca_v2.1$ | ✓ | — | — | — |
| N-type | $\alpha_{1B}$ | $Ca_v2.2$ | — | ✓ | ✓ | — |
| L-type | $\alpha_{1C}$ | $Ca_v1.2$ | — | — | — | ✓ |
| L-type | $\alpha_{1D}$ | $Ca_v1.3$ | — | — | — | ✓ |
| R-type | $\alpha_{1E}$ | $Ca_v2.3$ | — | — | — | — |
| L-type | $\alpha_{1F}$ | $Ca_v1.4$ | — | — | — | ✓ |
| T-type | $\alpha_{1G}$ | $Ca_v3.1$ | — | — | — | — |
| T-type | $\alpha_{1H}$ | $Ca_v3.2$ | — | — | — | — |
| T-type | $\alpha_{1I}$ | $Ca_v3.3$ | — | — | — | — |

Calcium channels have been shown to mediate the development and maintenance of the neuronal sensitization processes associated with neuropathic pain, and provide attractive targets for the development of analgesic drugs (reviewed in Vanegas, H., et al., *Pain* (2000) 85:9-18). All of the high-threshold Ca channel types are expressed in the spinal cord, and the contributions of L-, N and P/Q-types in acute nociception are currently being investigated. In contrast, examination of the functional roles of these channels in more chronic pain conditions strongly indicates a pathophysiological role for the N-type channel (reviewed in Vanegas, ibid).

Mutations in calcium channel $\alpha_1$ subunit genes in animals can provide important clues to potential therapeutic targets for pain intervention. Genetically altered mice null for the $\alpha_{1B}$ N-type calcium channel gene have been reported by several independent groups (Ino, M., et al., *Proc. Natl. Acad. Sci. USA* (2001) 98:5323-5328; Kim, C., et al., *Mol Cell Neurosci* (2001) 18:235-245; Saegusa, H., et al., *Proc. Natl. Acad. Sci. USA* (2001) 97:6132-6137); Hatakeyama, S., et al., *NeuroReport* (2001) 12:2423-2427). The $\alpha_{1B}$ N-type null mice were viable, fertile and showed normal motor coordination. In one study, peripheral body temperature, blood pressure and heart rate in the N-type gene knock-out mice were all normal (Saegusa, ibid). In another study, the baroreflex mediated by the sympathetic nervous system was reduced after bilateral carotid occlusion (Ino, ibid). In another study, mice were examined for other behavioral changes and were found to be normal except for exhibiting significantly lower anxiety-related behaviors (Saegusa, ibid), suggesting the N-type channel may be a potential target for mood disorders as well as pain. In all studies mice lacking functional N-type channels exhibit marked decreases in the chronic and inflammatory pain responses. In contrast, mice lacking N-type channels generally showed normal acute nociceptive responses.

Two examples of either FDA-approved or investigational drug that act on N-type channel are gabapentin and ziconotide. Gabapentin, 1-(aminomethyl)cyclohexaneacetic acid (Neurontin®), is an anticonvulsant originally found to be active in a number of animal seizure models (Taylor, C. P., et al., *Epilepsy Res*. (1998) 29:233-249). Subsequent work has demonstrated that gabapentin is also successful at preventing hyperalgesia in a number of different animal pain models, including chronic constriction injury (CCI), heat hyperalgesia, inflammation, diabetic neuropathy, static and dynamic mechanoallodynia associated with postoperative pain (Taylor, ibid; Cesena, R. M., *Neurosci Lett* (1999) 262:101-104; Field, M. J., et al., *Pain* (1999) 80:391-398; Cheng, J-K., et al. *Anesthesiology* (2000) 92:1126-1131; Nicholson, B., *Acta Neurol Scand* (2000) 101:359-371).

While its mechanism of action is incompletely understood, current evidence suggests that gabapentin does not directly interact with GABA receptors in many neuronal systems, but rather modulates the activity of high threshold calcium channels. Gabapentin has been shown to bind to the calcium channel $\alpha_2\delta$ ancillary subunit, although it remains to be determined whether this interaction accounts for its therapeutic effects in neuropathic pain.

In humans, gabapentin exhibits clinically effective antihyperalgesic activity against a wide ranging of neuropathic pain conditions. Numerous open label case studies and three large double blind trials suggest gabapentin might be useful in the treatment of pain. Doses ranging from 300-2400 mg/day were studied in treating diabetic neuropathy (Backonja, M., et al., *JAMA* (1998) 280:1831-1836), postherpetic neuralgia (Rowbotham, M., et al., *JAMA* (1998) 280:1837-1842), trigeminal neuralgia, migraine and pain associated with cancer and multiple sclerosis (Di Trapani, G., et al., *Clin Ter* (2000) 151:145-148; Caraceni, A., et al., *J Pain & Symp Manag* (1999) 17:441-445; Houtchens, M. K., et al., *Multiple Sclerosis* (1997) 3:250-253; see also Magnus, L., *Epilepsia* (1999) 40:S66-S72; Laird, M. A., et al., *Annal Pharmacotherap* (2000) 34:802-807; Nicholson, supra).

Ziconotide (Prialt®; SNX-111) is a synthetic analgesic derived from the cone snail peptide *Conus magus* MVIIA that has been shown to reversibly block N-type calcium channels. In a variety of animal models, the selective block of N-type channels via intrathecal administration of ziconotide significantly depresses the formalin phase 2 response, thermal hyperalgesia, mechanical allodynia and post-surgical pain (Malmberg, A. B., et al., *J Neurosci* (1994) 14:4882-4890; Bowersox, S, S., et al., *J Pharmacol Exp Ther* (1996) 279: 1243-1249; Sluka, K., A., *J Pharmacol Exp Ther* (1998) 287:232-237; Wang, Y-X., et al. *Soc Neurosci Abstr* (1998) 24:1626).

Ziconotide has been evaluated in a number of clinical trials via intrathecal administration for the treatment of a variety of conditions including post-herpetic neuralgia, phantom limb syndrome, HIV-related neuropathic pain and intractable cancer pain (reviewed in Mathur, V., S., *Seminars in Anesthesia, Perioperative medicine and Pain* (2000) 19:67-75). In phase II and III clinical trials with patients unresponsive to intrathecal opiates, ziconotide has significantly reduced pain scores and in a number of specific instances resulted in relief after many years of continuous pain. Ziconotide is also being examined for the management of severe post-operative pain as well as for brain damage following stroke and severe head trauma (Heading, C., *Curr Opin CPNS Investigational Drugs* (1999) 1:153-166). In two case studies ziconotide has been further examined for usefulness in the management of intractable spasticity following spinal cord injury in patients unresponsive to baclofen and morphine (Ridgeway, B., et al., *Pain* (2000) 85:287-289). In one instance, ziconotide decreased the spasticity from the severe range to the mild to none range with few side effects. In another patient ziconotide also reduced spasticity to the mild range although at the required dosage significant side effects including memory loss, confusion and sedation prevented continuation of the therapy.

T-type calcium channels are involved in various medical conditions. In mice lacking the gene expressing the $\alpha_{1G}$ subunit, resistance to absence seizures was observed (Kim, D., et al., *Neuron* (2001) 31:35-45). Other studies have also implicated the $\alpha_{1H}$ subunit in the development of epilepsy (Su, H., et al., *J Neurosci* (2002) 22:3645-3655). There is strong evidence that some existing anticonvulsant drugs, such as ethosuximide, function through the blockade of T-type channels (Gomora, J. C., et al., *Mol Pharmacol* (2001) 60:1121-1132).

Low voltage-activated calcium channels are highly expressed in tissues of the cardiovascular system. Mibefradil, a calcium channel blocker 10-30-fold selective for T-type over L-type channels, was approved for use in hypertension and angina. It was withdrawn from the market shortly after launch due to interactions with other drugs (Heady, T. N., et al., *Jpn J Pharmacol*. (2001) 85:339-350).

Growing evidence suggests T-type calcium channels may also be involved in pain. Both mibefradil and ethosuximide have shown anti-hyperalgesic activity in the spinal nerve ligation model of neuropathic pain in rats (Dogrul, A., et al., *Pain* (2003) 105:159-168).

U.S. Pat. Nos. 6,011,035; 6,294,533; 6,310,059; and 6,492,375; PCT publications WO 01375 and WO 01/45709; PCT publications based on PCT CA 99/00612, PCT CA 00/01586; PCT CA 00/01558; PCT CA 00/01557; PCT CA 2004/000535; and PCT CA 2004/000539, and U.S. patent application Ser. No. 10/746,932 filed 23 Dec. 2003; Ser. No. 10/746,933 filed 23 Dec. 2003; Ser. No. 10/409,793 filed 8 Apr. 2003; Ser. No. 10/409,868 filed 8 Apr. 2003; Ser. No. 10/655,393 filed 3 Sep. 2003; Ser. No. 10/821,584 filed 9 Apr. 2004; and Ser. No. 10/821,389 filed 9 Apr. 2004 disclose calcium channel blockers where a piperidine or piperazine ring is substituted by various aromatic moieties. These applications and publications are incorporated herein by reference.

U.S. Pat. No. 5,646,149 describes calcium channel antagonists of the formula A-Y-B wherein B contains a piperazine or piperidine ring directly linked to Y. An essential component of these molecules is represented by A, which must be an antioxidant; the piperazine or piperidine itself is said to be important. The exemplified compounds contain a benzhydril substituent, based on known calcium channel blockers (see below). U.S. Pat. No. 5,703,071 discloses compounds said to be useful in treating ischemic diseases. A mandatory portion of the molecule is a tropolone residue, with substituents such as piperazine derivatives, including their benzhydril derivatives. U.S. Pat. No. 5,428,038 discloses compounds indicated to exhibit a neural protective and antiallergic effect. These compounds are coumarin derivatives which may include derivatives of piperazine and other six-membered heterocycles. A permitted substituent on the heterocycle is diphenylhydroxymethyl. Thus, approaches in the art for various indications which may involve calcium channel blocking activity have employed compounds which incidentally contain piperidine or piperazine moieties substituted with benzhydril but mandate additional substituents to maintain functionality.

Certain compounds containing both benzhydril moieties and piperidine or piperazine are known to be calcium channel antagonists and neuroleptic drugs. For example, Gould, R. J., et al., *Proc. Natl. Acad. Sci. USA* (1983) 80:5122-5125 describes antischizophrenic neuroleptic drugs such as lidoflazine, fluspirilene, pimozide, clopimozide, and penfluridol. It has also been shown that fluspirilene binds to sites on L-type calcium channels (King, V. F., et al., *J Biol Chem* (1989) 264:5633-5641) as well as blocking N-type calcium current (Grantham, C. J., et al., *Brit J Pharmacol* (1944) 111:483-488). In addition, lomerizine, as developed by Kanebo, K. K., is a known calcium channel blocker. However, lomerizine is not specific for N-type channels. A review of publications concerning lomerizine is found in Dooley, D., *Current Opinion in CPNS Investigational Drugs* (1999) 1:116-125.

U.S. patent publication 2002/0019389 published 14 Feb. 2002 discloses what are characterized as urea derivatives useful as anticancer agents. Among these derivatives are piperazines wherein one ring nitrogen forms a urea with a benzhydril group. Certain of these compounds contain 3,5-dimethylphenyl or benzhydril coupled to the alternate piperazine nitrogen. These compounds are described simply as anticancer agents and are not reported to have any effects on calcium ion channels or any indications mediated by such channels.

The foregoing publications are listed for convenience, and are not to be construed as prior art.

DISCLOSURE OF THE INVENTION

The invention relates to compounds useful in treating conditions such as chronic and acute pain; mood disorders such as anxiety, depression, and addiction; gastrointestinal disorders such as inflammatory bowel disease and irritable bowel syndrome; genitourinary disorders such as urinary incontinence, interstitial colitis and sexual dysfunction; neuroprotection such as cerebral ischemia, stroke and traumatic brain injury; neurodegenerative disorders; metabolic disorders such as diabetes and obesity; cardiovascular disease; epilepsy; diabetes; certain types of cancer such as prostate cancer; sleep disorders; Parkinson's disease; psychosis such as schizophrenia; male birth control; and other indications associated with calcium metabolism, including synaptic calcium channel-mediated functions. The compounds of the invention are urea-containing derivatives of piperazine or aminopiperidine with substituents that enhance the calcium channel blocking activity of the compounds. Thus, in one aspect, the invention is directed to compounds of the formula

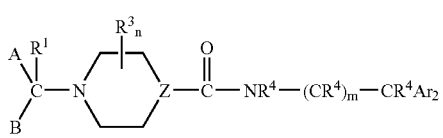

(1)

and salts or conjugates thereof, wherein each of A and B is independently a H, alkyl (1-8C), 6-membered aromatic or nonaromatic, carbocyclic moiety or cyclic moiety containing 1-2 heteroatoms or is an aminoalkyl or aminoalkenyl, and wherein one and only one of A and B may be H or alkyl (1-8C);

$R^1$ is H or alkyl (1-8C), alkenyl (2-8C) or alkynyl (2-8C);

Z is N or $CHNR^2$ wherein $R^2$ is H or alkyl (1-8C), alkenyl (2-8C) or alkynyl (2-8C);

each $R^3$ is independently a substituent selected from the group consisting of =O, alkyl (1-8C), alkenyl (2-8C), alkynyl (2-8C), acyl, aryl, alkylaryl, halo, $CHF_2$, $CF_3$, $OCF_3$, $OCHF_2$, OCOR, CN, $NO_2$, $NR_2$, OR, SR, COR, COOR, $CONR_2$, SOR, $SO_2R$, $SO_3R$, NRCOR, NROR, NRCOOR, $OCONR_2$, SONR, $SO_2NR$, OOCR, NRSOR and $NRSO_2R$, wherein R is H or alkyl (1-8C), alkenyl (2-8C), alkynyl (2-8C), aryl, or alkylaryl, wherein two R on the same N may form a 5-7 membered ring, and wherein two substituents on adjacent C may form a 5-7 membered ring;

wherein each $R^4$ is independently H or alkyl (1-4C);

m is 0-3;

n is 0-2;

each Ar is independently a 6-membered or fused aromatic ring system optionally containing 1-2 nitrogen atoms; and wherein each cyclic moiety included in A or B and each Ar moiety in formula (1) may be substituted by one or more substituents selected from the group consisting of =O (in nonaromatic cyclic moieties), alkyl (1-8C), alkenyl (2-8C), alkynyl (2-8C), acyl, aryl, alkylaryl, halo, $CHF_2$, $CF_3$, $OCF_3$, $OCHF_2$, OCOR, CN, $NO_2$, $NR_2$, OR, SR, COR, COOR, $CONR_2$, SOR, $SO_2R$, $SO_3R$, NRCOR, NROR, NRCOOR, $OCONR_2$, SONR, $SO_2NR$, OOCR, NRSOR and $NRSO_2R$, wherein R is H or alkyl (1-8C), alkenyl (2-8C), alkynyl (2-8C), aryl, or alkylaryl, wherein two R on the same N may form a 5-7 membered ring, and wherein two substituents on adjacent C may form a 5-7 membered ring, and wherein any alkyl, alkenyl, alkynyl or aryl set forth above may further be substituted by =O, alkyl (1-8C), alkenyl (2-8C), alkynyl (2-8C), acyl, aryl, alkylaryl, halo, $CHF_2$, $CF_3$, $OCF_3$, $OCHF_2$, OCOR, CN, $NO_2$, $NR_2$, OR, SR, COR, COOR, $CONR_2$, SOR, $SO_2R$, $SO_3R$, NRCOR, NROR, NRCOOR, $OCONR_2$, SONR, $SO_2NR$, OOCR, NRSOR and $NRSO_2R$, wherein R is H or alkyl (1-8C), alkenyl (2-8C), alkynyl (2-8C), aryl, or alkylaryl, wherein two R on the same N may form a 5-7 membered ring, and wherein two substituents on adjacent C may form a 5-7 membered ring;

with the provisos that if Z is N, $R^1$ and all $R^4$ are H, m is 0 or 1 and each Ar is unsubstituted phenyl, A and B cannot both be unsubstituted phenyl.

The invention is also directed to methods to modulate calcium channel activity, preferably N-type and T-type channel activity, using the compounds of formula (1) wherein the definition of such compound is as above, but does not include the proviso set forth above, and wherein A and/or B may contain more than 2 nitrogen atoms. These compounds, thus, can be used to treat certain undesirable physiological conditions; these conditions are associated with calcium channel activity. The invention is also directed to the use of these compounds for the preparation of medicaments for the treatment of conditions requiring modulation of calcium channel activity, including anxiety, depression, and addiction; gastrointestinal disorders such as inflammatory bowel disease and irritable bowel syndrome; genitourinary disorders such as urinary incontinence, interstitial colitis and sexual dysfunction; neuroprotection such as cerebral ischemia, stroke and traumatic brain injury; neurodegenerative disorders; metabolic disorders such as diabetes and obesity; cardiovascular disease; epilepsy; diabetes; certain types of cancer such as prostate cancer; sleep disorders; Parkinson's disease; psychosis such as schizophrenia; male birth control. In another aspect, the invention is directed to pharmaceutical compositions containing the compounds of formula (1).

MODES OF CARRYING OUT THE INVENTION

The compounds of formula (1) including compounds where A and/or B may have more than 2 nitrogen atoms in the ring and wherein the provisos do not apply are useful in the methods of the invention and exert their desirable effects through their ability to modulate the activity of N-type and/or T-type calcium channels. This makes them useful for treatment of certain conditions. Conditions where modulation of N-type calcium channels is desired include: chronic and acute pain; mood disorders such as anxiety, depression, and addiction; neurodegenerative disorders; gastrointestinal disorders such as inflammatory bowel disease and irritable bowel syndrome; genitourinary disorders such as urinary incontinence, interstitial colitis and sexual dysfunction; neuroprotection such as cerebral ischemia, stroke and traumatic brain injury; and metabolic disorders such as diabetes and obesity. Conditions where modulation of T-type calcium channels is desired include: cardiovascular disease; epilepsy; diabetes; certain types of cancer such as prostate cancer; chronic and acute pain; sleep disorders; Parkinson's disease; psychosis such as schizophrenia; and male birth control.

Acute pain includes but is not limited to nociceptive pain and post-operative pain. Chronic pain includes but is not limited by: peripheral neuropathic pain such as post-herpetic neuralgia, diabetic neuropathic pain, neuropathic cancer pain, failed back-surgery syndrome, trigeminal neuralgia, and phantom limb pain; central neuropathic pain such as multiple sclerosis related pain, Parkinson disease related pain, post-stroke pain, post-traumatic spinal cord injury pain, and pain in dementia; musculoskeletal pain such as osteoarthritic pain and fibromyalgia syndrome; inflammatory pain such as rheumatoid arthritis and endometriosis; headache such as migraine, cluster headache, tension headache syndrome, facial pain, headache caused by other diseases; visceral pain such as interstitial cystitis, irritable bowel syndrome and chronic pelvic pain syndrome; and mixed pain such as lower back pain, neck and shoulder pain, burning mouth syndrome and complex regional pain syndrome.

Anxiety includes but is not limited to the following conditions: generalized anxiety disorder, social anxiety disorder, panic disorder, obsessive-compulsive disorder, and post-traumatic stress syndrome. Addiction includes but is not limited to dependence, withdrawal and/or relapse of cocaine, opioid, alcohol and nicotine.

Neurodegenerative disorders include Parkinson's disease, Alzheimer's disease, multiple sclerosis, neuropathies, Huntington's disease and amyotrophic lateral sclerosis (ALS).

Cardiovascular disease includes but is not limited to hypertension, pulmonary hypertension, arrhythmia (such as atrial fibrillation and ventricular fibrillation), congestive heart failure, and angina pectoris.

Epilepsy includes but is not limited to partial seizures such as temporal lobe epilepsy, absence seizures, generalized seizures, and tonic/clonic seizures.

While the compounds described above generally have this activity, availability of this class of calcium channel modulators permits a nuanced selection of compounds for particular disorders. The availability of this class of compounds provides not only a genus of general utility in indications that are affected by calcium channel activity, but also provides a large number of compounds which can be mined and manipulated for specific interaction with particular forms of calcium channels. The availability of recombinantly produced calcium channels of the $\alpha_{1A}$-$\alpha_{1I}$ and $\alpha_{1S}$ types set forth above, facilitates this selection process. Dubel, S. J., et al., *Proc. Natl. Acad. Sci. USA* (1992) 89:5058-5062; Fujita, Y., et al., *Neuron* (1993) 10:585-598; Mikami, A., et al., *Nature* (1989) 340: 230-233; Mori, Y., et al., *Nature* (1991) 350:398-402; Snutch, T. P., et al., *Neuron* (1991) 7:45-57; Soong, T. W., et al., *Science* (1993) 260:1133-1136; Tomlinson, W. J., et al., *Neuropharmacology* (1993) 32:1117-1126; Williams, M. E., et al., *Neuron* (1992) 8:71-84; Williams, M. E., et al., *Science* (1992) 257:389-395; Perez-Reyes, et al., *Nature* (1998) 391: 896-900; Cribbs, L. L., et al., *Circulation Research* (1998) 83:103-109; Lee, J. H., et al., *Journal of Neuroscience* (1999) 19:1912-1921; McRory, J. E., et al., *Journal of Biological Chemistry* (2001) 276:3999-4011.

It is known that calcium channel activity is involved in a multiplicity of disorders, and particular types of channels are associated with particular conditions. The association of N-type and T-type channels in conditions associated with neural transmission would indicate that compounds of the invention which target N-type receptors are most useful in these conditions. Many of the members of the genus of compounds of formula (1) exhibit high affinity for N-type channels and/or T-type channels. Thus, as described below, they are screened for their ability to interact with N-type and/or T-type channels as an initial indication of desirable function. It is desirable that the compounds exhibit $IC_{50}$ values of <1 µM. The $IC_{50}$ is the concentration which inhibits 50% of the calcium, barium or other permeant divalent cation flux at a particular applied potential.

There are three distinguishable types of calcium channel inhibition. The first, designated "open channel blockage," is conveniently demonstrated when displayed calcium channels are maintained at an artificially negative resting potential of about −100 mV (as distinguished from the typical endogenous resting maintained potential of about −70 mV). When the displayed channels are abruptly depolarized under these conditions, calcium ions are caused to flow through the channel and exhibit a peak current flow which then decays. Open channel blocking inhibitors diminish the current exhibited at the peak flow and can also accelerate the rate of current decay.

This type of inhibition is distinguished from a second type of block, referred to herein as "inactivation inhibition." When maintained at less negative resting potentials, such as the physiologically important potential of −70 mV, a certain percentage of the channels may undergo conformational change, rendering them incapable of being activated—i.e., opened—by the abrupt depolarization. Thus, the peak current due to calcium ion flow will be diminished not because the open channel is blocked, but because some of the channels are unavailable for opening (inactivated). "Inactivation" type inhibitors increase the percentage of receptors that are in an inactivated state.

A third type of inhibition is designated "resting channel block". Resting channel block is the inhibition of the channel that occurs in the absence of membrane depolarization, that would normally lead to opening or inactivation. For example, resting channel blockers would diminish the peak current amplitude during the very first depolarization after drug application without additional inhibition during the depolarization.

In order to be maximally useful in treatment, it is also helpful to assess the side reactions which might occur. Thus, in addition to being able to modulate a particular calcium channel, it is desirable that the compound has very low activity with respect to the HERG $K^+$ channel which is expressed in the heart. Compounds that block this channel with high potency may cause reactions which are fatal. Thus, for a compound that modulates the calcium channel, it should also be shown that the HERG K+ channel is not inhibited. Similarly, it would be undesirable for the compound to inhibit cytochrome p450 since this enzyme is required for drug detoxification. Finally, the compound will be evaluated for calcium ion channel type specificity by comparing its activity among the various types of calcium channels, and specificity for one particular channel type is preferred. The compounds which progress through these tests successfully are then examined in animal models as actual drug candidates.

The compounds of the invention modulate the activity of calcium channels; in general, said modulation is the inhibition of the ability of the channel to transport calcium. As described below, the effect of a particular compound on calcium channel activity can readily be ascertained in a routine assay whereby the conditions are arranged so that the channel is activated, and the effect of the compound on this activation (either positive or negative) is assessed. Typical assays are described hereinbelow.

The Invention Compounds

The substituents on the basic structures of formula (1) are described above. Substituents in general include, but are not limited to, alkyl, alkenyl, alkynyl, aryl, arylalkyl, acyl, =O, halo, $CHF_2$, $CF_3$, $OCF_3$, $OCHF_2$, CN, $NO_2$, OR, $NR_2$, SR, SOR, $SO_2R$, $SO_3R$, OCOR, NRCOR, NROR, $NRCONR_2$, NRCOOR, $OCONR_2$, COR, COOR, NRSOR, $NRSO_2R$, $CONR_2$, SONR, and $SO_2NR_2$ (wherein each R is independently H or alkyl (1-8C), alkenyl (2-8C), alkenyl (2-8C), aryl or arylalkyl), —CN, —$CF_3$, and $NO_2$, and like substituents. Two substituents on the same N or adjacent C can form a 5-7 membered ring.

As used herein, the term "alkyl," "alkenyl" and "alkynyl" include straight-chain, branched-chain and cyclic monovalent substituents, containing only C and H when they are unsubstituted or unless otherwise noted. Examples include methyl, ethyl, isobutyl, cyclohexyl, cyclopentylethyl, 2-propenyl, 3-butynyl, and the like. Typically, the alkyl, alkenyl and alkynyl substituents contain 1-8C (alkyl) or 2-8C (alkenyl or alkynyl). Preferably they contain 1-6C or 1-4C (lower alkyl) or 2-6C or 2-4C (lower alkenyl or lower alkynyl).

Heteroalkyl, heteroalkenyl and heteroalkynyl are similarly defined but may contain one or more O, S or N heteroatoms or combinations thereof within the backbone residue.

As used herein, "acyl" encompasses the definitions of alkyl, alkenyl, alkynyl, each of which is coupled to an additional residue through a carbonyl group. Heteroacyl includes the related heteroforms.

"Aromatic" moiety or "aryl" moiety refers to a monocyclic or fused bicyclic moiety such as phenyl or naphthyl; "heteroaromatic" also refers to monocyclic or fused bicyclic ring systems containing one or more heteroatoms selected from O, S and N. The inclusion of a heteroatom permits inclusion of 5-membered rings to be considered aromatic as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Because tautomers are theoretically possible, phthalimido is also considered aromatic. Any monocyclic or fused ring bicyclic system which has the characteristics of aromaticity in terms of electron distribution throughout the ring system is included in this definition. Typically, the ring systems contain 5-12 ring member atoms.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of 1-8C, or the hetero forms thereof. These carbon chains may also include a carbonyl group, thus making them able to provide substituents as an acyl or heteroacyl moiety.

In general, any alkyl, alkenyl, alkynyl, acyl, or aryl (including the heteroforms) group contained in a substituent may itself optionally be substituted by additional substituents. The nature of these substituents is similar to those recited with regard to the primary substituents themselves. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments. However, alkyl substituted by aryl, amino, alkoxy, and the like would be included.

In the compounds of the invention, Ar is preferably a 6-membered or fused aromatic ring system optionally containing 1-2 nitrogen atoms. More preferably, Ar is an optionally substituted phenyl, 2-, 3- or 4-pyridyl, indolyl, 2- or 4-pyrimidyl, pyridazinyl, benzothiazolyl or benzimidazolyl. Even more preferably Ar is phenyl, pyridyl, or pyrimidyl. Most preferably Ar is phenyl. Each of these embodiments may optionally be substituted with one or more groups defined above, such as alkyl, alkenyl, alkynyl, aryl, O-aryl, O-alkylaryl, O-aroyl, NR-aryl, N-alkylaryl, NR-aroyl, halo, OR, $NR_2$, SR, OOCR, RCO, COOR, $CONR_2$, and/or $SO_2NR_2$, wherein each R is independently H or alkyl (1-8C), alkenyl (2-8C), alkynyl (2-8C), aryl or alkylaryl, and/or by —CN, —$CF_3$, and/or $NO_2$. Alkyl, alkenyl, alkynyl and aryl portions of these may be further substituted by similar substituents.

Among preferred substituents on Ar are alkyl, $CF_3$, $CHF_2$, OR, SR, $NR_2$, where R is as above-defined, and halo. Preferred embodiments of $R^1$ are methyl and H. Preferred embodiments of $R^3$ include =O and carboxy.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Suitable pharmaceutically acceptable acids and bases are well-known in the art, such as hydrochloric, sulphuric, citric, or tartaric acids and potassium hydroxide, sodium hydroxide, ammonium hydroxide, caffeine, various amines, and the like. Methods for preparation of the appropriate salts are well-established in the art.

In some cases, the compounds of the invention contain one or more chiral centers. The invention includes the isolated stereoisomeric forms as well as mixtures of stereoisomers in varying degrees of chiral purity.

In addition, the compounds of the invention may be coupled through conjugation to substances designed to alter the pharmacokinetics, for targeting, or for other reasons. Thus, the invention further includes conjugates of these compounds. For example, polyethylene glycol is often coupled to substances to enhance half-life; the compounds may be coupled to liposomes covalently or noncovalently or to other particulate carriers. They may also be coupled to targeting agents such as antibodies or peptidomimetics, often through linker moieties. Thus, the invention is also directed to the compounds of formula (1) when modified so as to be included in a conjugate of this type.

Synthesis of the Invention Compounds

The compounds of the invention may be synthesized using conventional methods.

Reaction Scheme 1 is illustrative and may be used to prepare compounds with piperazine rings adjacent C═O. The piperidine analog can be substituted and reaction of the nitrogen of CHNH$_2$ substitutes for the nitrogen of piperazine.

Reaction Scheme 1

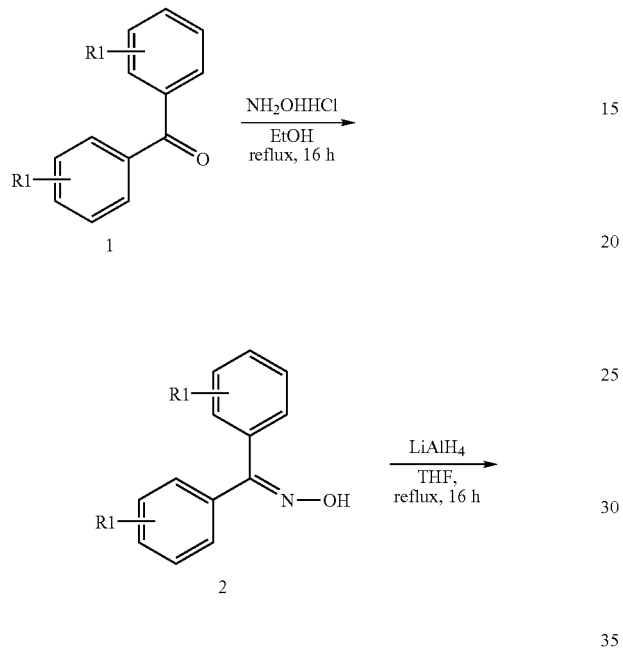

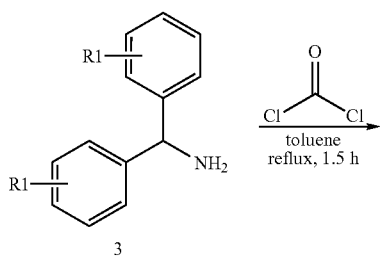

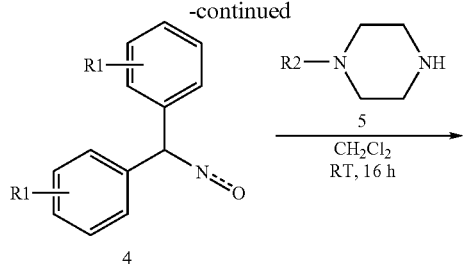

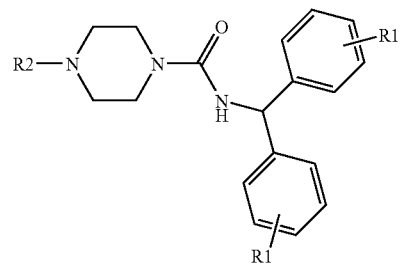

Reaction scheme 1 illustrates the general synthesis where R$^4$ is H, m and n are 0, and both Ar are phenyl. In preferred embodiments, piperazine compound 5 is for example benzhydryl piperazine, 1-(3-dimethylamino propyl)piperazine, 1-(3-piperidin-1-yl propyl)piperazine, 1-(3-morphonlino propyl)piperazine, 1(3-pyrrolidino propyl)piperazine. Reaction scheme 2 illustrates the synthesis when A and B are both phenyl and R1 is H.

Reaction Scheme 2

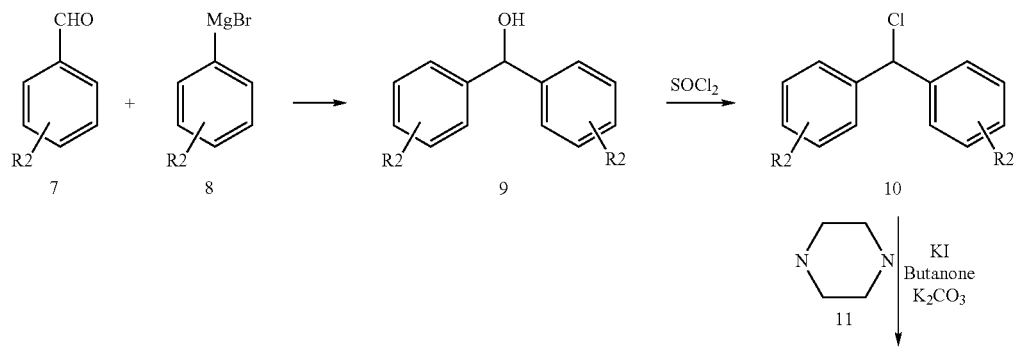

-continued

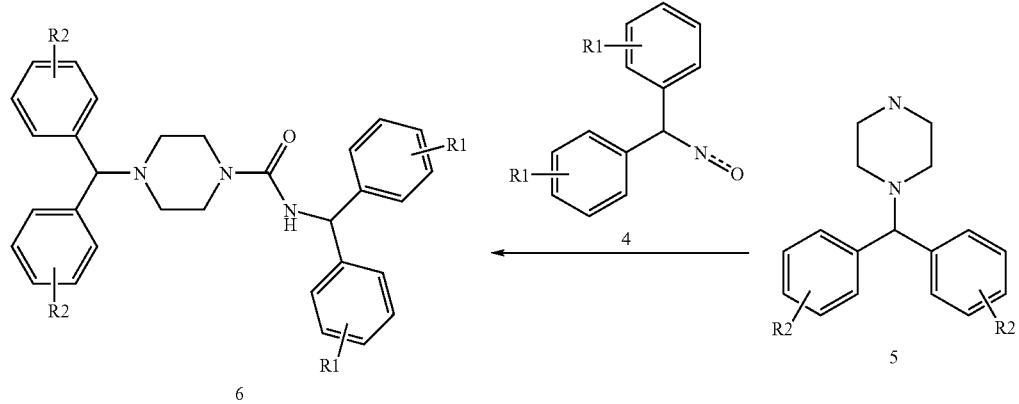

A similar sequence of reactions is applicable for the remaining embodiments of the invention. In scheme 2, the initial Grignard reaction to diphenyl methanol is followed by halogenation, generating a leaving group to be replaced by the ring N of piperazine or the 4-amino group of 4-amino piperidine having N at position 1 protected. The resulting compound 5 is reacted with benzhydril isocyanate to obtain the final product.

Libraries and Screening

The compounds of the invention can be synthesized individually using methods known in the art per se, or as members of a combinatorial library.

Synthesis of combinatorial libraries is now commonplace in the art. Suitable descriptions of such syntheses are found, for example, in Wentworth, Jr., P., et al., *Current Opinion in Biol.* (1993) 9:109-115; Salemme, F. R., et al., *Structure* (1997) 5:319-324. The libraries contain compounds with various substituents and various degrees of unsaturation, as well as different chain lengths. The libraries, which contain, as few as 10, but typically several hundred members to several thousand members, may then be screened for compounds which are particularly effective against a specific subtype of calcium channel, i.e., the N-type channel. In addition, using standard screening protocols, the libraries may be screened for compounds which block additional channels or receptors such as sodium channels, potassium channels and the like.

Methods of performing these screening functions are well known in the art. These methods can also be used for individually ascertaining the ability of a compound to agonize or antagonize the channel. Typically, the channel to be targeted is expressed at the surface of a recombinant host cell such as human embryonic kidney cells. The ability of the members of the library to bind the channel to be tested is measured, for example, by the ability of the compound in the library to displace a labeled binding ligand such as the ligand normally associated with the channel or an antibody to the channel. More typically, ability to antagonize the channel is measured in the presence of calcium, barium or other permeant divalent cation and the ability of the compound to interfere with the signal generated is measured using standard techniques. In more detail, one method involves the binding of radiolabeled agents that interact with the calcium channel and subsequent analysis of equilibrium binding measurements including, but not limited to, on rates, off rates, $K_d$ values and competitive binding by other molecules.

Another method involves the screening for the effects of compounds by electrophysiological assay whereby individual cells are impaled with a microelectrode and currents through the calcium channel are recorded before and after application of the compound of interest.

Another method, high-throughput spectrophotometric assay, utilizes loading of the cell lines with a fluorescent dye sensitive to intracellular calcium concentration and subsequent examination of the effects of compounds on the ability of depolarization by potassium chloride or other means to alter intracellular calcium levels.

As described above, a more definitive assay can be used to distinguish inhibitors of calcium flow which operate as open channel blockers, as opposed to those that operate by promoting inactivation of the channel or as resting channel blockers. The methods to distinguish these types of inhibition are more particularly described in the examples below. In general, open-channel blockers are assessed by measuring the level of peak current when depolarization is imposed on a background resting potential of about −100 mV in the presence and absence of the candidate compound. Successful open-channel blockers will reduce the peak current observed and may accelerate the decay of this current. Compounds that are inactivated channel blockers are generally determined by their ability to shift the voltage dependence of inactivation towards more negative potentials. This is also reflected in their ability to reduce peak currents at more depolarized holding potentials (e.g., −70 mV) and at higher frequencies of stimulation, e.g., 0.2 Hz vs. 0.03 Hz. Finally, resting channel blockers would diminish the peak current amplitude during the very first depolarization after drug application without additional inhibition during the depolarization.

Utility and Administration

For use as treatment of human and animal subjects, the compounds of the invention can be formulated as pharmaceutical or veterinary compositions. Depending on the subject to be treated, the mode of administration, and the type of treatment desired—e.g., prevention, prophylaxis, therapy; the compounds are formulated in ways consonant with these parameters. A summary of such techniques is found in *Remington's Pharmaceutical Sciences*, latest edition, Mack Publishing Co., Easton, Pa., incorporated herein by reference.

In general, for use in treatment, the compounds of formula (1) may be used alone, as mixtures of two or more compounds of formula (1) or in combination with other pharmaceuticals. An example of other potential pharmaceuticals to combine with the compounds of formula (1) would include pharmaceuticals for the treatment of the same indication but having a different mechanism of action from N-type or T-type calcium channel blocking. For example, in the treatment of pain, a compound of formula (1) may be combined with another pain relief treatment such as an NSAID, or a compound which selectively inhibits COX-2, or an opioid, or an adjuvant analgesic such as an antidepressant. Another example of a potential pharmaceutical to combine with the compounds of formula (1) would include pharmaceuticals for the treatment of different yet associated or related symptoms or indications. Depending on the mode of administration, the compounds will be formulated into suitable compositions to permit facile delivery.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as is understood in the art.

For administration to animal or human subjects, the dosage of the compounds of the invention is typically 0.1-15 mg/kg, preferably 0.1-1 mg/kg. However, dosage levels are highly dependent on the nature of the condition, drug efficacy, the condition of the patient, the judgment of the practitioner, and the frequency and mode of administration.

The following examples are intended to illustrate but not to limit the invention.

EXAMPLE 1

Synthesis of 4-Benzhydryl-piperazine-1-carboxylic acid benzhydryl amide

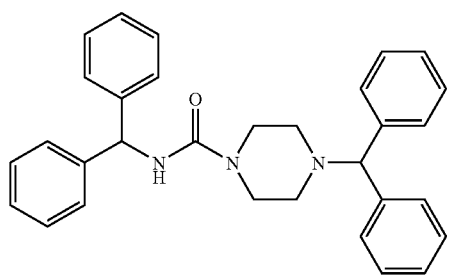

To a solution of diphenylmethyl piperazine (0.3 g, 1.18 mmol) in dry $CH_2Cl_2$ (10 ml) was added diphenylmethyl isocyanate (0.22 ml, 1.18 mmol) drop wise under nitrogen. The resulting mixture was stirred at room temperature over night. Removal of solvent under reduced pressure followed by column chromatography using hexane:ethyl acetate (3:1) gives the desired product in 80% yield.

EXAMPLE 2

Synthesis of 4-(1-Methyl-piperidin-4-ylmethyl)-piperazin-1-carboxylic acid benzhydryl-amide

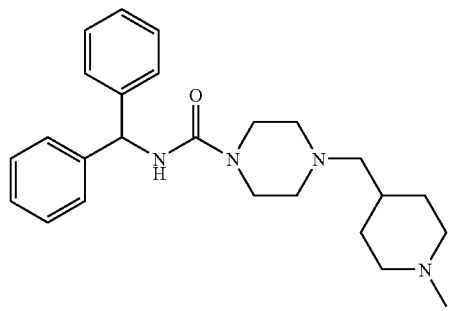

To a solution of 1-(1-methyl-piperidin-4-ylmethyl)-piperazine (0.5 g, 2.7 mmol) in dry $CH_2Cl_2$ (12 ml) was added diphenylmethyl isocyanate (0.56 ml, 2.7 mmol) drop wise under nitrogen. The resulting mixture was stirred at room temperature over night. Removal of solvent under reduced pressure followed by column chromatography using $CH_2Cl_2$:$CH_3OH$ (10:1) gives the desired product in 82% yield.

EXAMPLE 3

Synthesis of N-Benzhydryl-4-((phenyl)(1-methylpiperidin-4-yl)methyl)piperazine-1-carboxamide

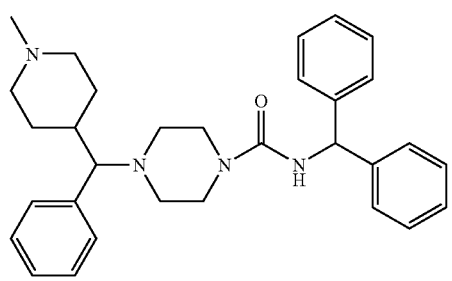

A. Synthesis of 1-Methylpiperidin-4-yl phenyl methanone

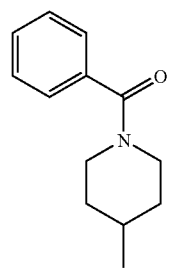

1-Methylpiperidine-4-carboxylic acid hydrochloride salt 10 g (55.7 mmol) was added to thionyl chloride (25 ml) and stirred at room temperature until the solid dissolved completely. The reaction mixture was stirred for another 20 minutes and concentrated. The product was used for the next step without further purification.

To a cooled suspension of anhydrous aluminum chloride (20 g, 75 mmol) in benzene 30 ml at 0° C. was added 1-methylpiperidine-4-carboxylic acid chloride in small portions and the resulted mixture was refluxed for 3 hours. The reaction mixture was cooled down, poured into ice water. The organic phase was discarded. The aqueous solution was washed with 2×50 ml ethyl ether, basified with potassium hydroxide pellet slowly to pH>10 and extracted with ethyl ether 4×50 ml. The combined ethereal solution was dried over sodium sulfate and concentrated to give 9.5 g of the title compound in 84% yield.

B. Synthesis of 1-Methylpiperidin-4-yl phenyl methanol

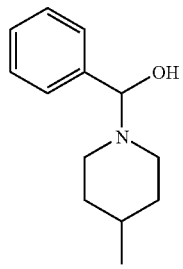

To a solution of 1-methylpiperidin-4-yl phenyl methanone 1.02 g (5 mmol) in 30 ml methanol was added in small portions sodium borohydride 0.378 g (10 mmol). The reaction mixture was stirred at room temperature for two hours, concentrated, added water and extracted with methylene chloride 2×50 ml. The combined organic solution was dried over sodium sulfate and concentrated to give 1 g of the title compound in 98% yield.

C. Synthesis of 4-(Chloro)phenylmethyl)-1-methylpiperidine

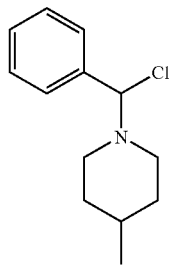

To a solution of 4-chlorophenyl 1-methylpiperidin-4-yl methanol 1.2 g (5.85 mmol) in toluene (5 ml) was added thionyl chloride (0.5 ml) dropwise. The resulting mixture was stirred at room temperature over night. The mixture was then made alkaline with NaOH solution and extracted with ethyl acetate (3×40). The combined organic solution was dried and concentrated to give 1.2 g of desired product.

D. Synthesis of 1-(Phenyl)(1-methylpiperidin-4-yl)methyl)piperazine

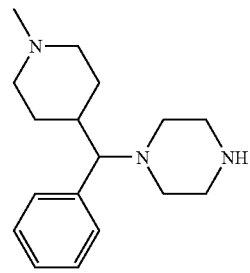

A mixture of 4-(chloro(phenyl)methyl)-1-methylpiperidine (1.2 g, 5.38 mmol) in butanone (10 ml), anhydrous piperazine (1.9 g, 21.52 mmol), anhydrous $K_2CO_3$ (0.74 g, 5.38 mmol) and KI (0.89 g, 5.38 mmol) was refluxed under nitrogen for 18 hours. The mixture was then cooled and filtered and the solvent removed in vacuo. The residue was dissolved in $CH_2Cl_2$ (50 ml) and washed with water (30 ml). Drying and removal of the solvent followed by chromatography ($CH_2Cl_2$:$CH_3OH$:$NH_4OH$ 90:10:0.5) afforded desired product in 70% yield.

E. Synthesis of N-Benzhydryl-4-((phenyl)(1-methylpiperidin-4-yl)methyl)piperazine-1-carboxamide

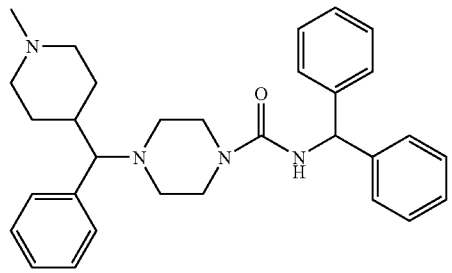

To a solution of 1-((phenyl)(1-methylpiperidin-4-yl)methyl)piperazine 0.1 g (0.36 mmol) dissolved in methylene chloride (20 ml) was added diphenylmethyl isocyanate 0.075 g (0.36 mmol) and the reaction mixture was stirred at room temperature for 1 hour. The reaction mixture was washed with saturated sodium bicarbonate solution and brine, dried over sodium sulfate and concentrated. The residue was applied to flash column chromatography using methylene chloride and methanol (100:10) as eluents to give 0.15 g of desired product.

EXAMPLE 4

Synthesis of N-Benzhydryl-4-(1-(phenyl)-1-(1-methylpiperidin-4-yl)ethyl)piperazine-1-carboxamide

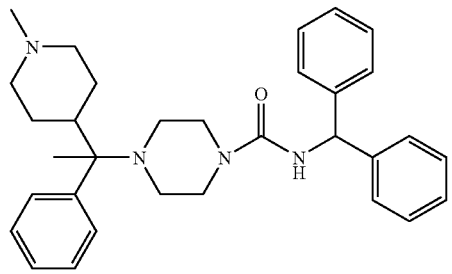

A. Synthesis of Tert-butyl 4-[cyano(1-methylpiperidin-4-yl)phenylmethyl]piperazine-1-carboxylate

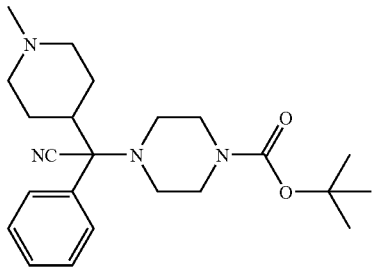

A solution of 1-methyl-4-piperidinyl phenyl methanone 1.218 g (6 mmol), N-Boc piperazine 1.118 g (6 mmol) and titanium (IV) isoproxide 1.77 ml (6 mmol) in 1,2-dichloroethane (25 ml) was stirred at room temperature for 72 hours. Diethylaluminum cyanide (1M solution in toluene) 12 ml was added and the reaction mixture was stirred for another 24 hours. The reaction was quenched with saturated sodium bicarbonate solution (20 ml) and filtered. The filtrate was extracted with ethyl acetate twice. The combined ethyl acetate solution was washed with more saturated sodium bicarbonate solution and brine, dried over sodium sulfate, concentrated and applied to flash column chromatography using methylene chloride and methanol (100:2.5) as eluent to give 0.6 g of desired product in 25% yield.

B. Synthesis of Tert-butyl 4-[1-(1-methylpiperidin-4-yl0-1-phenylethyl]piperazine-1-carboxylate

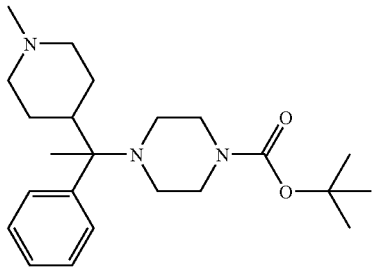

A solution of tert-butyl 4-[cyano(1-methylpiperidin-4-yl)phenylmethyl]piperazine-1-carboxylate 0.6 g (1.511 mmol) dissolved in THF (10 ml) was added dropwise to methyl magnesium bromide (3M solution in ethyl ether) 3.2 ml at 0° C. under nitrogen protection. The reaction mixture was then stirred at room temperature overnight. The reaction was quenched with water, concentrated and partitioned between ethyl acetate and saturated sodium bicarbonate. The ethyl acetate solution was washed with brine and dried over sodium sulfate. After concentration, the oily residue was applied to flash column chromatography using methylene chloride and methanol (100:3) as eluents to give 0.16 g of desired product (27% yield).

C. Synthesis of 1-[1-(1-methylpiperidin-4-yl)-1-phenylethyl]piperazine

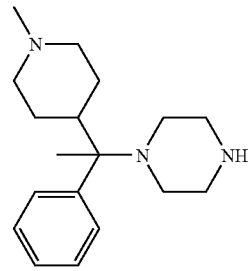

To a solution of tert-butyl 4-[1-(1-methylpiperidin-4-yl)-1-phenylethyl]piperazine-1-carboxylate 0.16 g (0.41 mmol) in methylene chloride (20 ml) was added trifluoroacetic acid (5 ml) and resulting mixture stirred at room temperature for 2 hours. The reaction mixture was concentrated, dissolved in methylene chloride and washed with saturated sodium bicarbonate and brine. The methylene chloride solution was dried over sodium sulfate and concentrated to give 0.1 g (yield 82%) of desired product.

D. Synthesis of N-Benzhydryl-4-(1-(phenyl)-1-(1-methylpiperidin-4-yl)ethyl)piperazine-1-carboxamide

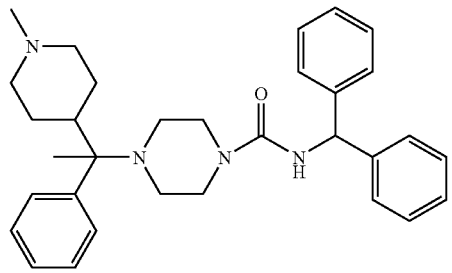

To a solution of 1-[1-(1-methylpiperidin-4-yl)-1-phenylethyl]piperazine 0.1 g (0.348 mmol) dissolved in methylene chloride (20 ml) was added diphenylmethyl isocyanate 0.073 g (0.348 mmol) and the reaction mixture was stirred at room temperature for 1 hour. The reaction mixture was washed with saturated sodium bicarbonate solution and brine, dried over sodium sulfate and concentrated. The residue was applied to flash column chromatography using methylene chloride and methanol (100:10) as eluents to give 0.15 g of desired product in 87% yield.

EXAMPLE 5

Synthesis of N-benzhydryl-4-((4-chlorophenyl)(1-methylpiperidin-4-yl)methyl)piperazine-1-carboxamide

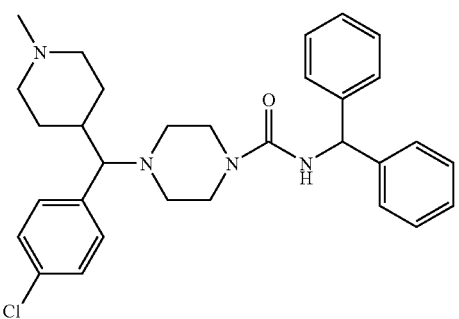

A. Synthesis of 1-Methylpiperidine-4-carboxylic acid chloride

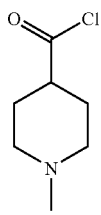

1-Methylpiperidine-4-carboxylic acid hydrochloride salt 10 g (55.7 mmol) was added to thionyl chloride (25 ml) and resulting mixture stirred at room temperature until the solid dissolved completely. The reaction mixture was stirred for another 20 minutes and concentrated. The product was used for the next step without further purification.

B. Synthesis of 4-Chlorophenyl-1-methylpiperidin-4-yl methanone

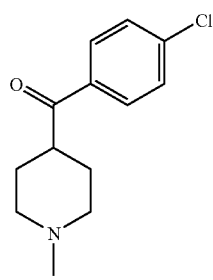

To a cold suspension of anhydrous aluminum chloride (20 g, 75 mmol) in chlorobenzene 30 ml at 0° C. was added 1-methylpiperidine-4-carboxylic acid chloride in small portions and the resulted mixture was refluxed for 3 hours. The reaction mixture was cooled down, poured into ice water. The organic phase was discarded. The aqueous solution was washed with 2×50 ml ethyl ether, basified with potassium hydroxide pellet slowly to pH>10 and extracted with ethyl ether 4×50 ml. The combined organic solution was dried over sodium sulfate and concentrated to give 11.2 g of desired product in 85% yield.

C. Synthesis of (4-Chlorophenyl)(1-methylpiperidine-4-yl)methanol

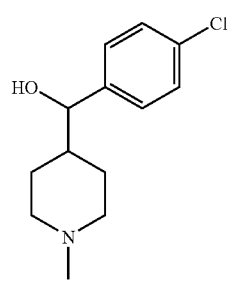

To a solution of 4-chlorophenyl 1-methylpiperidin-4-yl methanone 1.19 g (5 mmol) in 30 ml methanol was added in small portions sodium borohydride 0.378 g (10 mmol). The reaction mixture was stirred at room temperature for two hours, concentrated, added water and extracted with methylene chloride 2×50 ml. The combined organic solution was dried over sodium sulfate and concentrated to give 1.2 g of desired product in 98% yield.

D. Synthesis of 4-(Chloro(4-chlorophenyl)methyl)-1-methylpiperidine

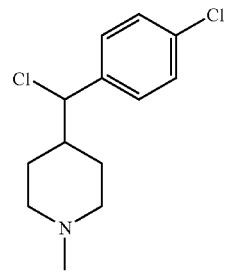

To a solution of 4-chlorophenyl 1-methylpiperidin-4-yl methanol 1.2 g (5.02 mmol) in toluene (5 ml) was added thionyl chloride (0.45 ml) dropwise. The resulting mixture was stirred at room temperature over night. The mixture was then made alkaline with NaOH solution and extracted with ethyl acetate (3×40). The combined organic solution was dried and concentrated to give 1.2 g of desired product.

E. Synthesis of 1-((4-chlorophenyl)(1-methylpiperidin-4-yl)methyl)piperazine

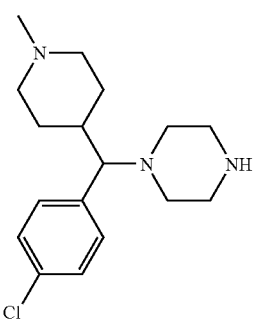

A mixture of 4-(chloro(4-chlorophenyl)methyl)-1-methylpiperidine (1.2 g, 4.66 mmol) in butanone (10 ml), anhydrous piperazine (1.58 g, 18.45 mmol), anhydrous $K_2CO_3$ (0.63 g, 4.61 mmol) and KI (0.76 g, 4.61 mmol) was refluxed under nitrogen for 18 hours. The mixture was then cooled and filtered and the solvent removed in vacuo. The residue was dissolved in $CH_2Cl_2$ (50 ml) and washed with water (30 ml). Drying and removal of the solvent followed by chromatography ($CH_2Cl_2$:$CH_3OH$:$NH_4OH$ 90:10:0.5) afforded desired product in 62% yield.

F. Synthesis of N-benzhydryl-4-((4-chlorophenyl)(1-methylpiperidin-4-yl)methyl)piperazine-1-carboxamide

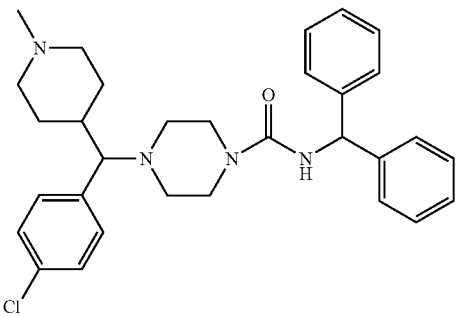

To a solution of 1-((4-chlorophenyl)(1-methylpiperidin-4-yl)methyl)piperazine 0.1 g (0.325 mmol) dissolved in methylene chloride (20 ml) was added diphenylmethyl isocyanate 0.07 μg (0.325 mmol) and the reaction mixture was stirred at room temperature for 1 hour. The reaction mixture was washed with saturated sodium bicarbonate solution and brine, dried over sodium sulfate and concentrated. The residue was applied to flash column chromatography using methylene chloride and methanol (100:10) as eluents to give 0.14 g of desired product.

EXAMPLE 6

Synthesis of N-benzhydryl-4-((4-fluorophenyl)(1-methylpiperidin-4-yl)methyl)piperazine-1-carboxamide

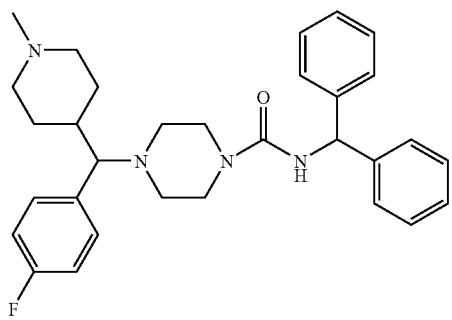

A. Synthesis of 4-Fluorophenyl-1-methylpiperidin-4-yl methanone

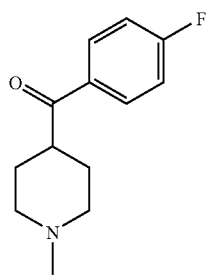

4-Fluorophenyl piperidin-4-yl methanone 1.79 g (8.66 mmol) was added to formic acid (1.5 ml) and formaldehyde 1.05 ml and the reaction mixture was stirred at 55-60° C. for 3 hours. After cooled down, water was added, basified with potassium hydroxide pellets to pH>10 and extracted with ethyl ether 3×50 ml. The combined organic solution was dried over sodium sulfate and concentrated to give 1.88 g of desired product in 98% yield.

B. Synthesis of 4-Fluorophenyl 1-methylpiperidin-4-yl methanol

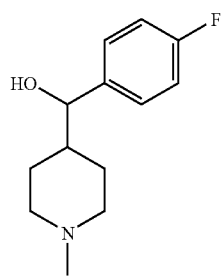

To a solution of 4-fluorophenyl 1-methylpiperidin-4-yl methanone 1.10 g (5 mmol) in 30 ml methanol was added in small portions sodium borohydride 0.378 g (10 mmol). The reaction mixture was stirred at room temperature for two hours, concentrated, added water and extracted with methylene chloride 2×50 ml. The combined organic solution was dried over sodium sulfate and concentrated to give 1.0 g of desired product in 90% yield.

C. Synthesis of 4-(Chloro(4-fluorophenyl)methyl)-1-methylpiperidine

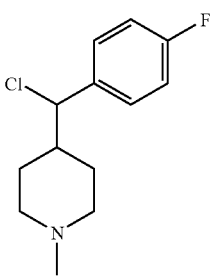

To a solution of 4-fluorophenyl 1-methylpiperidin-4-yl methanol 1.2 g (4.98 mmol) in toluene (5 ml) was added thionyl chloride (0.44 ml) dropwise. The resulting mixture was stirred at room temperature over night. The mixture was then made alkaline with NaOH solution and extracted with ethyl acetate (3×40). The combined organic solution was dried and concentrated to give 1.1 g of desired product.

D. Synthesis of 1-((4-Fluorophenyl)(1-methylpiperidin-4-yl)methyl)piperazine

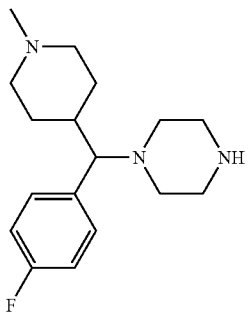

A mixture of 4-(chloro(4-fluorophenyl)methyl)-1-methylpiperidine (1.2 g, 4.12 mmol) in butanone (10 ml), anhydrous piperazine (1.43 g, 16.48 mmol), anhydrous K2CO3 (0.54 g, 4.14 mmol) and KI (0.65 g, 4.14 mmol) was refluxed under nitrogen for 18 hours. The mixture was then cooled and filtered and the solvent removed in vacuo. The residue was dissolved in CH2Cl2 (50 ml) and washed with water (30 ml). Drying and removal of the solvent followed by chromatography (CH2Cl2:CH$_3$OH:NH4OH 90:10:0.5) afforded desired product in 62% yield.

E. Synthesis of N-benzhydryl-4-((4-fluorophenyl)(1-methylpiperidin-4-yl)methyl)piperazine-1-carboxamide

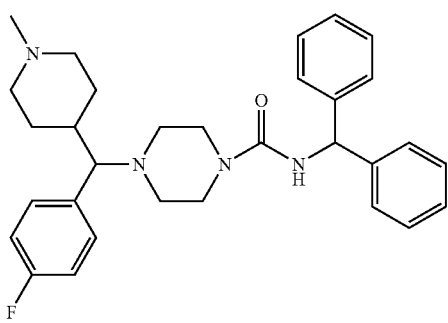

To a solution of 1-((4-fluorophenyl)(1-methylpiperidin-4-yl)methyl)piperazine 0.1 g (0.343 mmol) dissolved in methylene chloride (20 ml) was added diphenylmethyl isocyanate 0.073 g (0.343 mmol) and the reaction mixture was stirred at room temperature for 1 hour. The reaction mixture was washed with saturated sodium bicarbonate solution and brine, dried over sodium sulfate and concentrated. The residue was applied to flash column chromatography using methylene chloride and methanol (100:10) as eluents to give 0.13 g of desired product.

EXAMPLE 7

Synthesis of N-benzhydryl-4-((S)-1-(1-methylpyrrolidin-2-ylmethyl)piperazine-1-carboxamide

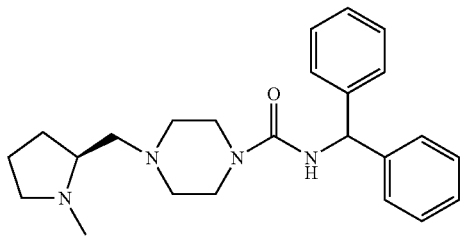

A. Synthesis of (S)-tert-butyl 2-(4-benzylpiperazine-1-carbonyl)pyrrolidine-1-carboxylate

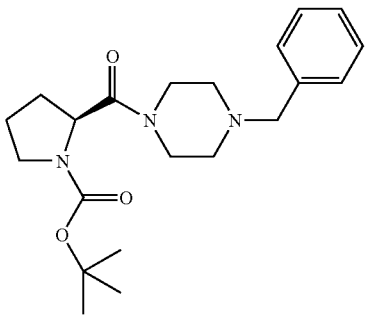

A solution of N-Boc-L-proline 0.645 g (3 mmol), 1-benzylpiperazine 0.528 g (3 mmol), 1-ethyl-3-(3-dimethylaminopropyl)carbodiimide hydrochloride (EDC) 1.152 g (6 mmol) and catalytic amount of 4-(dimethylamino) pyridine in methylene chloride (50 ml) was stirred at room temperature overnight. The reaction mixture was concentrated and applied to flash column chromatography using methylene chloride and methanol (100:5) as eluents to give 1.01 g of desired product in 90% yield.

B. Synthesis of (S)-1-benzyl-4-[(1-methylpyrrolidin-2-yl)methyl]piperazine

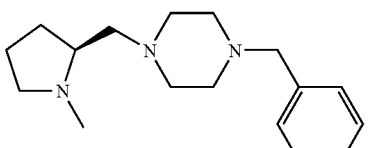

(S)-tert-butyl 2-(4-benzylpiperazine-1-carbonyl)pyrrolidine-1-carboxylate 1.01 g (2.71 mmol) in THF (10 ml) was added slowly to a solution of 1M lithium aluminum hydride in THF (8.2 ml) at 0° C. under argon protection. The reaction mixture was refluxed for 2 hours, cooled, quenched with water and extracted with ethyl ether 2×50 ml. The combined organic solution was washed with brine, dried over sodium sulfate and concentrated to give 0.71 g of desired product in 96% yield.

C. Synthesis of (S)-1-(1-methylpyrrolidin-2-yl methyl)piperazine

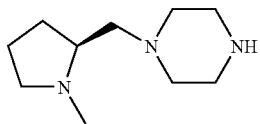

To a solution of (S)-1-benzyl-4-[(1-methylpyrrolidin-2-yl) methyl]piperazine 0.71 g (2.61 mmol) in 40 ml THF was added 10% Pd/C 0.4 g and exposed to 1 atm hydrogen overnight. The reaction mixture was filtered. The filtrate was concentrated to give 0.450 g of desired product in 94% yield.

D. Synthesis of N-benzhydryl-4-((S)-1-(1-methylpyrrolidin-2-yl methyl)piperazine-1-carboxamide

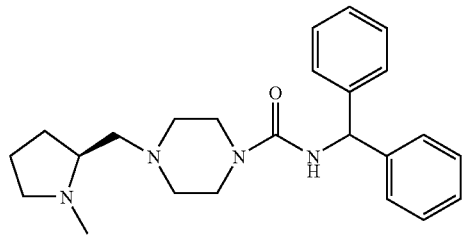

To a solution of (S)-1-(1-methylpyrrolidin-2-yl methyl) piperazine 0.225 g (1.23 mmol) in methylene chloride (30 ml) was added diphenylmethyl isocyanate 0.257 g (1.23 mmol). The reaction mixture was stirred at room temperature for 30 minutes, concentrated and applied to flash chromatography using methylene chloride and methanol (100:5) as eluents to give 0.33 g of desired product in 68% yield.

EXAMPLE 8

Synthesis of N-benzhydryl-4-((S)-1-(1-methylpiperidinyl-2-yl methyl)piperazine-1-carboxamide

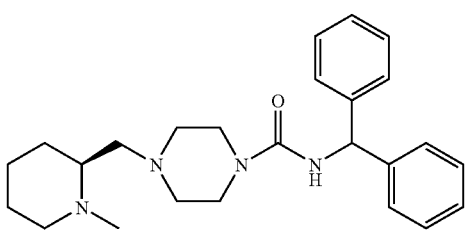

A. Synthesis of (S)-tert-butyl 2-(4-benzylpiperazine-1-carbonyl)piperidine-1-carboxylate

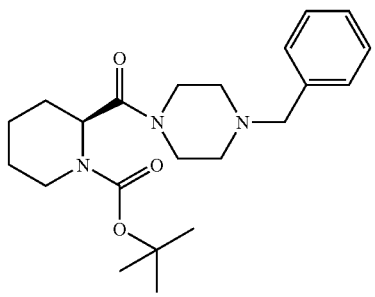

A solution of (S)-(−)-1-Boc-2-piperidine carboxylic acid 1 g (4.27 mmol), 1-benzylpiperazine 0.77 g (4.27 mmol), EDC 1.64 g (8.54 mmol) and catalytic amount of 4-(dimethylamino)pyridine in methylene chloride (50 ml) was stirred at room temperature overnight. The reaction mixture was concentrated and applied to flash column chromatography using methylene chloride and methanol (100:5) as eluents to give 1.23 g of desired product in 74.5% yield.

B. Synthesis of (S)-1-benzyl-4-[(1-methylpiperidin-2-yl)methyl]piperazine

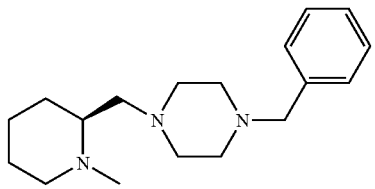

A solution of (S)-tert-butyl 2-(4-benzylpiperazine-1-carbonyl)piperidine-1-carboxylate 1.23 g (3.18 mmol) in THF (10 ml) was added slowly to a solution of 1M lithium aluminum hydride in THF 9.6 ml in THF (8 ml) at 0° C. under argon protection. The reaction mixture was refluxed for 2 hours, cooled down, quenched with water and extracted with ethyl ether 2×50 ml. The combined organic solution was washed with brine, dried over sodium sulfate and concentrated to give 0.87 g of desired product 95% yield.

C. Synthesis of (S)-1-(1-methylpiperidin-2-yl methyl)piperazine

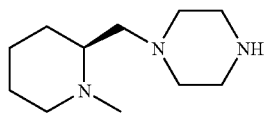

To a solution of (S)-1-benzyl-4-[(1-methylpiperidin-2-yl) methyl]piperazine 0.87 g (3.03 mmol) in THF (40 ml) was added 10% Pd/C 0.4 g and exposed to 1 atm hydrogen overnight. The reaction mixture was filtered. The filtrate was concentrated 0.3 g of desired product in 50% yield.

D. Synthesis of N-benzhydryl-4-((S)-1-(1-methylpiperidinyl-2-yl methyl)piperazine-1-carboxamide

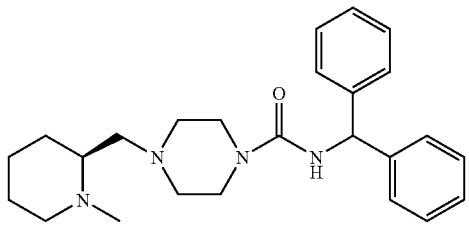

To a solution of (S)-1-(1-methylpiperidin-2-yl methyl)piperazine 0.3 g (1.52 mmol) in methylene chloride (30 ml) was added diphenylmethyl isocyanate 0.318 g (1.52 mmol). The reaction mixture was stirred at room temperature for 30 minutes, concentrated and applied to flash chromatography using methylene chloride and methanol (100:5) as eluents 0.33 g of desired product in 53% yield.

EXAMPLE 9

Synthesis of Isocyanates

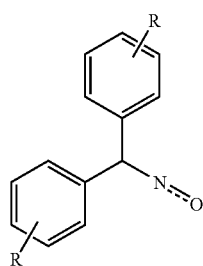

The following isocyanates were made following the procedure outlined below for 3,3'-difluorophenyl methyl isocyanate: 4,4'-dimethylphenyl methyl isocyanate; 4,4'-difluorophenyl methyl isocyanate; and 4,4'-dichlorophenyl methyl isocyanate.

A. Synthesis of 3,3'-difluorophenyl methyl hydroxylamine

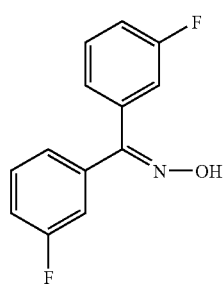

3,3'-Difluorobezophenone (5 g, 20.1 mmol) and hydroxylamine hydrochloride (5 g, 71.9 mmol) were dissolved in ethanol (200 mL) and refluxed for 16 h. The crude reaction was evaporated to dryness in vacuo and then taken up in $CH_2Cl_2$. The organic phase was washed with water, dried over $Na_2SO_4$ and dried under vacuum. The desired product was purified by silica gel chromatography ($CH_2Cl_2$, $R_f$ 0.3) as a white solid (3.63 g, 77%).

B. Synthesis of 3,3'-difluorophenyl methyl amine

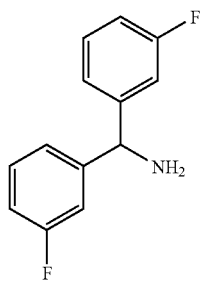

3,3'-Difluorophenyl methyl hydroxylamine (3.63 g, 15.6 mmol) was dissolved in THF (50 mL) under a $N_2$ atmosphere. $LiAlH_4$ (1.24 g, 32.6 mmol) was added portion-wise as a solid. The reaction was refluxed gently for 16 h under $N_2$. The reaction was quenched by the addition of 10% NaOH to give the formation of a white precipitate. The solid was removed by suction filtration and washed with EtOAc. The organic layer was dried ($Na_2SO_4$) and concentrated in vacuo. The crude residue was purified by silica gel chromatography ($CH_2Cl_2$ to 10% $EtOAc/CH_2Cl_2$, $R_f$ 0.1 to 0.6) to give a dark yellow oil (2 g, 58%).

C. Synthesis of 3,3'-difluorophenyl methyl isocyanate

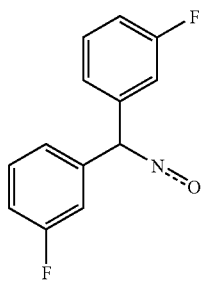

3,3'-Difluorophenyl methyl amine was dissolved in toluene (15 mL) under a $N_2$ atmosphere. Phosgene (9 mL of a 20% solution in toluene) was added dropwise. The reaction was refluxed under $N_2$ for 1.5 h. The solvent was removed under reduced pressure. The remaining residue was dried under hi-vac for 2 h prior to use.

EXAMPLE 10

Synthesis of N-[bis(4-methylphenyl)methyl]-4-(3-dimethylaminopropyl)piperazine-1-carboxamide

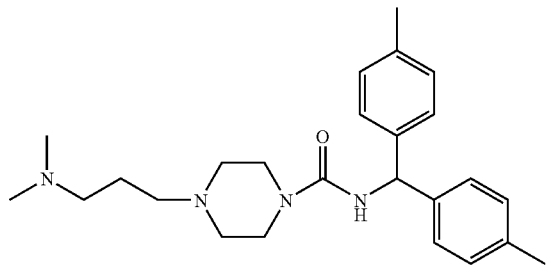

4,4'-Dimethyl phenyl methyl isocyanate (140 mg, 0.59 mmol) (prepared as provided in Example 9) was dissolved in CH$_2$Cl$_2$ (5 mL). 1-(3-Dimethylamino propyl)piperazine (92 mg, 0.53 mmol) in CH$_2$Cl$_2$ (5 mL) was added and the reaction was stirred for 16 h at room temperature under N$_2$. After 16 h, the solvent was removed under reduced pressure. The crude residue was purified by silica gel chromatography Oct. 10, 1980 Et$_3$N/MeOH/EtOAc (R$_f$ 0.4) to give the product as a clear oil (120 mg, 55%). The HCl salt was obtained by dissolving the product in CH$_2$Cl$_2$ followed by the addition of HCl/Et$_2$O to give a white precipitate. The excess HCl and solvent was removed in vacuo to yield the product as white solid. MS (C$_{25}$H$_{36}$N$_4$O+1) 409.4.

EXAMPLE 11

Synthesis of N-[bis(4-chlorophenyl)methyl]-4-(3-piperidin-1-yl propyl)piperazine-1-carboxamide

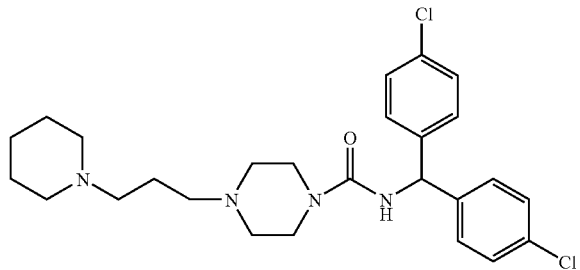

4,4'-Dichloro phenyl methyl isocyanate (275 mg, 0.99 mmol) (prepared as provided in Example 9) was dissolved in CH$_2$Cl$_2$ (5 mL). 1-(3-Piperidin-1-yl propyl)piperazine (190 mg, 0.89 mmol) in CH$_2$Cl$_2$ (5 mL) was added and the reaction was stirred for 16 h at room temperature under N$_2$. After 16 h, the solvent was removed under reduced pressure. The crude residue was purified by silica gel chromatography May 5, 1990 Et$_3$N/MeOH/EtOAc (R$_f$ 0.2) to give the product as a clear oil (260 mg, 60%). The HCl salt was obtained by dissolving the product in CH$_2$Cl$_2$ followed by the addition of HCl/Et$_2$O to give a white precipitate. The excess HCl and solvent was removed in vacuo to yield the product as white solid. MS (C$_{26}$H$_{34}$Cl$_2$N$_4$O) 489.4.

EXAMPLE 12

N-[bis(4-fluorophenyl)methyl]-4-(3-morpholin-4-yl propyl)piperazine-1-carboxamide

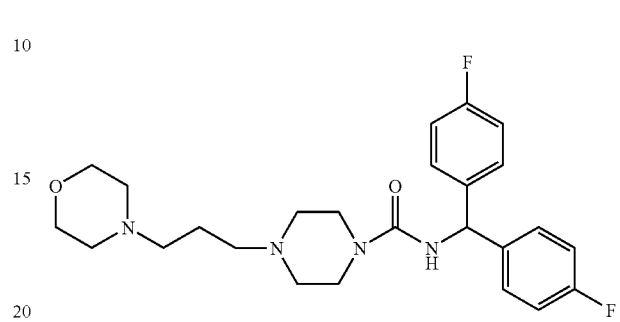

4,4'-Difluoro phenyl methyl isocyanate (250 mg, 1.03 mmol) (prepared as provided in example 9) was dissolved in CH$_2$Cl$_2$ (5 mL). 1-(3-morpholino propyl)piperazine (150 mg, 7 mmol) in CH$_2$Cl$_2$ (5 mL) was added and the reaction was stirred for 16 h at room temperature under N$_2$. After 16 h, the solvent was removed under reduced pressure. The crude residue was purified by silica gel chromatography Oct. 10, 1980 Et$_3$N/MeOH/EtOAc (R$_f$ 0.4) to give the product as a clear oil (300 mg, 86%). The HCl salt was obtained by dissolving the product in CH$_2$Cl$_2$ followed by the addition of HCl/Et$_2$O to give a white precipitate. The excess HCl and solvent was removed in vacuo to yield the product as white solid. MS (C$_{25}$H$_{32}$F$_2$N$_4$O$_2$-1) 457.3.

EXAMPLE 13

N-[bis(4-fluorophenyl)methyl]-4-(3-pyrrolidin-1-yl propyl)piperazine-1-carboxamide

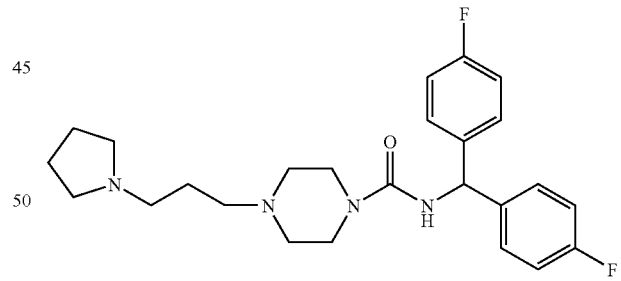

4,4'-Difluoro phenyl methyl isocyanate (250 mg, 1.03 mmol) (prepared as provided in example 9) was dissolved in CH$_2$Cl$_2$ (5 mL). 1-(3-Pyrrolidinyl propyl)piperazine (184 mg, 9 mmol) in CH$_2$Cl$_2$ (5 mL) was added and the reaction was stirred for 16 h at room temperature under N$_2$. After 16 h, the solvent was removed under reduced pressure. The crude residue was purified by silica gel chromatography Oct. 10, 1980 Et$_3$N/MeOH/EtOAc (R$_f$ 0.4) to give the product as a clear oil (300 mg, 73%). The HCl salt was obtained by dissolving the product in CH$_2$Cl$_2$ followed by the addition of HCl/Et$_2$O to give a white precipitate. The excess HCl and solvent was removed in vacuo to yield the product as white solid. MS (C$_{25}$H$_{32}$F$_2$N$_4$O+1) 443.4.

EXAMPLE 14

Synthesis of N-benzhydryl-4-((1-methyl-4-phenylpiperidin-4-yl)methyl)piperazine-1-carboxamide

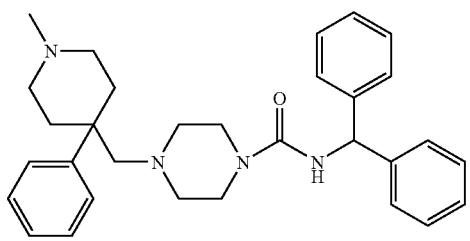

A. Synthesis of 1-methyl-4-phenylpiperidine-4-carbonitrile

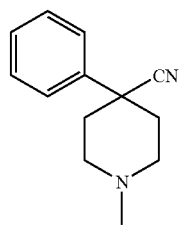

To a solution of mechlorethamine (4 g, 25.6 mmol) and benzyl cyanide (4 g, 34.2 mmol) in toluene (25 ml) was added sodium amide (2 g, 51.2 mmol) at 40-50° C. in portions for 1 hour. The reaction mixture was heated to reflux about 2 hours after the addition. The reaction mixture was cooled to room temperature and washed with saturated sodium bicarbonate solution and brine, dried over sodium sulfate and concentrated. The residue was applied to flash column chromatography using methylene chloride and methanol (100:5) as eluents to give 3 g of desired product.

B. Synthesis of 1-methyl-4-phenylpiperidine-4-carboxylic acid hydrochloride

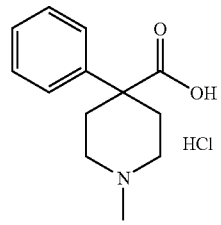

1-Methyl-4-phenylpiperidine-4-carbonitrile (3 g, 15 mmol) was refluxed with 6N HCl (40 ml) overnight. The reaction mixture was concentrated to remove water. The desired product (3.4 g) was obtained by heating and drying under vacuum in the oven.

C. Synthesis of (4-benzylpiperazin-1-yl)(1-methyl-4-phenylpiperidin-4-yl)methanone

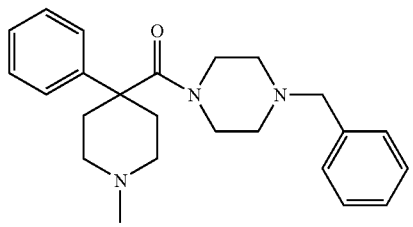

A solution of 1-methyl-4-phenylpiperidine-4-carboxylic acid hydrochloride (1.35 g, 5 mmol), benzyl piperazine 0.88 g (5 mmol), triethylamine 1 ml and EDC 1.91 g (10 mmol) and DMAP (catalytic) in 40 ml dichloromethane was stirred at room temperature overnight, concentrated, added water and extracted with ethyl acetate 2'50 ml. The combined organic solution was dried over sodium sulfate and concentrated. The residue was applied to flash column chromatography using methylene chloride and methanol (100:10) as eluents to give 1.5 g of desired product.

D. Synthesis of 1-Benzyl-4-((1-methyl-4-phenylpiperidin-4-yl)methyl)piperazine

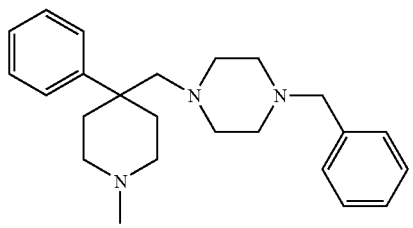

To a solution of (4-benzylpiperazin-1-yl)(1-methyl-4-phenylpiperidin-4-yl)methanone (1.5 g, 4 mmol) in THF (30 ml) was added LiAlH$_4$ (8 mmol) in portions. The resulting mixture was stirred at room temperature overnight. The mixture was quenched with ethyl acetate and methanol then made alkaline with 10% NaOH solution and extracted with ethyl acetate (3×40). The combined organic solution was dried and concentrated to give 1.5 g of desired product.

E. Synthesis of 1-((1-methyl-4-phenylpiperidin-4-yl)methyl)piperazine

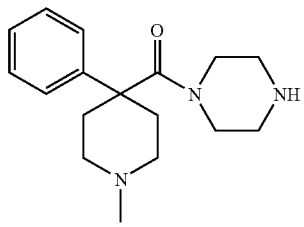

A mixture of 1-benzyl-4-((1-methyl-4-phenylpiperidin-4-yl)methyl)piperazine (1.5 g, 4 mmol) and 20% PdOH/C in methanol (50 ml) was shaken in the hydrogenation bar under H₂ 50-60 psi for 18 hours. The mixture was then filtered and the solvent removed in vacuo to afford desired product.

F. Synthesis of N-benzhydryl-4-((1-methyl-4-phenylpiperidin-4-yl)methyl)piperazine-1-carboxamide

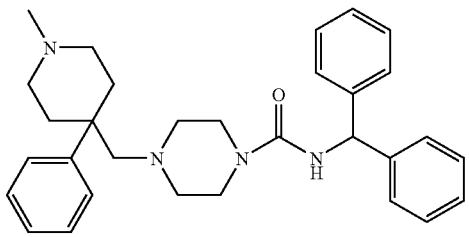

To a solution of 1-((methyl-4-phenylpiperidin-4-yl)methyl)piperazine (0.135 g, 0.5 mmol) dissolved in methylene chloride (5 ml) was added diphenylmethyl isocyanate (0.115 g, 0.55 mmol) and the reaction mixture was stirred at room temperature for 1 hour. The reaction mixture was washed with saturated sodium bicarbonate solution and brine, dried over sodium sulfate and concentrated. The residue was applied to flash column chromatography using methylene chloride and methanol (100:10) as eluents to give 0.13 g of desired product.

EXAMPLE 15

Synthesis of N-benzhydryl-2,6-dimethyl-4-((1-methylpiperidin-4-yl)methyl)piperazine-1-carboxamide

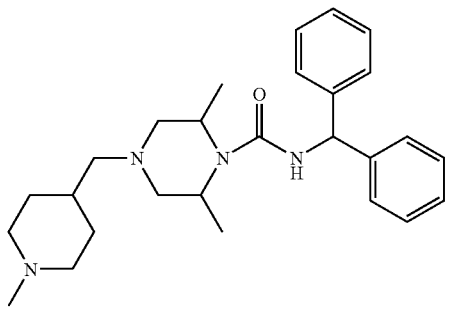

A. Synthesis of 1-(Tert-butyoxycarbonyl)piperidine-4-methylcarboxylate

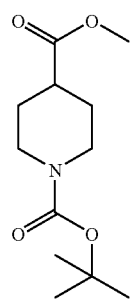

A solution of isonipecotate (7.2 g, 50 mmol), Boc anhydride (12 g, 55 mmol), triethylamine 7 ml and in 80 ml methanol was stirred at room temperature overnight, concentrated, added water and extracted with ethyl acetate 2×50 ml. The combined organic solution was dried over sodium sulfate and concentrated. The residue was applied to flash column chromatography using ethyl acetate: petroleum ether (3:1) as eluents to give 12 g of desired product.

B. Synthesis of 1-(tert-butoxycarbonyl)piperidine-4-carboxylic acid

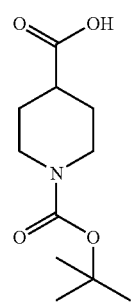

A mixture of 1-(tert-butoxycarbonyl)piperidine-4-methylcarboxylate (2.42 g, 10 mmol) and LiOH. 3H₂O in THF (45 ml) water (15 ml) and methanol (15 ml) was stirred at room temperature overnight. The mixture was then concentrated to remove the solvent. The residue was adjust to pH-2 with 2N HCl and extracted with ethyl acetate (2×40 ml). The combined organic solution was dried with sodium sulfate and concentrated to give 2.3 g of desired product.

C. Synthesis of tert-butyl 4-(3,5-dimethylpiperazine-1-carbonyl)piperidine-1-carboxylate

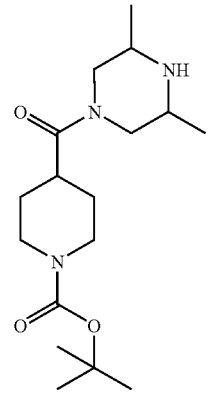

A solution of 1-(tert-butoxycarbonyl)piperidine-4-carboxylic acid (2.3 g, 10 mmol), 2,6-dimethylpiperazine (1.14 g, 10 mmol), and EDC (3.82 g, 20 mmol) and DMAP (catalytic) in 20 ml dichloromethane was stirred at room temperature overnight, concentrated, added water and extracted with ethyl acetate 2×50 ml. The combined organic solution was dried over sodium sulfate and concentrated. The residue was applied to flash column chromatography using methylene chloride and methanol (100:5) as eluents to give 1.9 g of desired product.

D. Synthesis of 3,5-dimethyl-1-((1-methylpiperidin-4-yl)methyl)piperazine

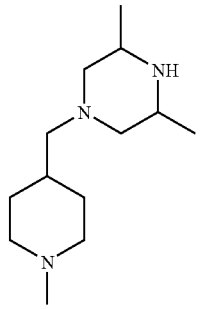

To a solution of tert-butyl-4-(3,5-dimethylpiperazine-1-carbonyl)piperidine-1-carboxylate (1.9 g, 5.8 mmol) in THF (50 ml) was added LiAlH$_4$ (18.7 mmol) in portions. The resulting mixture was stirred at room temperature overnight. The mixture was quenched with ethyl acetate and methanol then made alkaline with 10% NaOH solution and extracted with ethyl acetate (3×40). The combined organic solution was dried and concentrated to give 1.2 g of desired product.

E. Synthesis of N-benzhydryl-2,6-dimethyl-4-((1-methylpiperidin-4-yl)methyl)piperazine-1-carboxamide

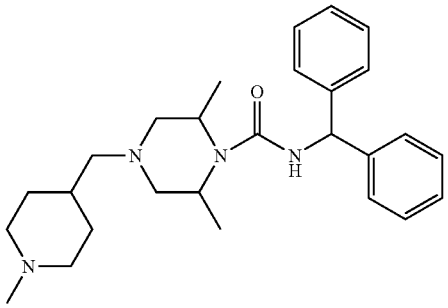

To a solution of 3,5-dimethyl-1-((1-methylpiperidin-4-yl)methyl)piperazine (0.2 g, 1 mmol) dissolved in methylene chloride (5 ml) was added diphenylmethyl isocyanate (0.227 g, 1.09 mmol) and the reaction mixture was stirred at room temperature for 1 hour. The reaction mixture was washed with saturated sodium bicarbonate solution and brine, dried over sodium sulfate and concentrated. The residue was applied to flash column chromatography using methylene chloride and methanol (100:10) as eluents to give 0.12 g of desired product.

EXAMPLE 16

Following the procedures set forth above, the following compounds were prepared:

| Compound No. | Name | Structure |
|---|---|---|
| 1 | 4-Benzhydryl-piperazine-1-carboxylic acid benzhydryl-amide | 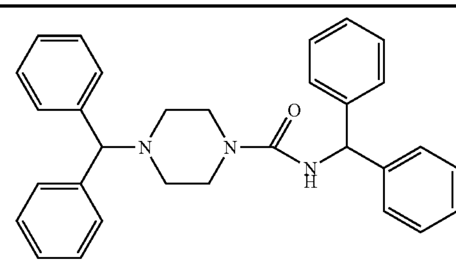 |
| 2 | 4-[(2,4-Dichloro-phenyl)-phenyl-methyl]-piperazine-1-carboxylic acid benzhydryl-amide | 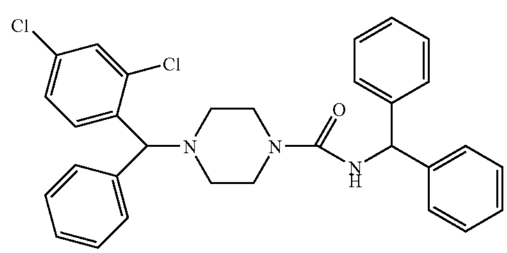 |

-continued

| Compound No. | Name |
|---|---|
| 3 | 4-[2,4-Dimethyl-phenyl)-phenyl-methyl]-piperazine-1-carboxylic acid benzhydryl-amide |
| 4 | 4-[(4-Chloro-phenyl)-phenyl-methyl]-piperazine-1-carboxylic acid benzhydryl-amide |
| 5 | 4-[(3-Chloro-phenyl)-phenyl-methyl]-piperazine-1-carboxylic acid benzhydryl-amide |
| 6 | 4-[(2-Chloro-phenyl)-phenyl-methyl]-piperazine-1-carboxylic acid benzhydryl-amide |
| 7 | 4-[(2,3-Dichloro-phenyl)-phenyl-methyl]-piperazine-1-carboxylic acid benzhydryl-amide |
| 8 | 4-(Benzo[1,3]dioxol-5-yl-phenyl-methyl)-piperazine-1-carboxylic acid benzhydryl-amide |

-continued

| Compound No. | Name | Structure |
|---|---|---|
| 9 | 4-[(4-Methoxy-phenyl)-(4-trifluoromethyl-phenyl)-methyl]-piperazine-1-carboxylic acid benzhydryl-amide | 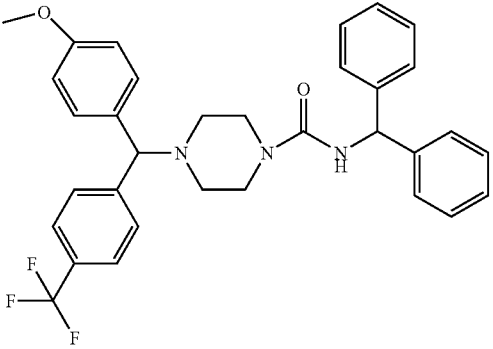 |
| 10 | 4-(1-Methyl-piperidin-4-yl-methyl)-piperazine-1-carboxylic acid benzhydryl-amide | 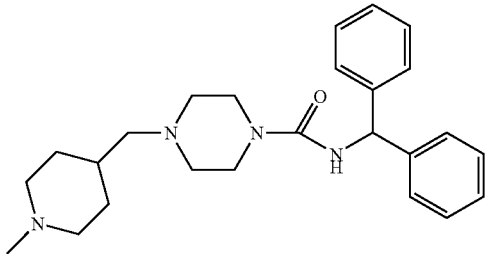 |
| 11 | 4-(3-Dimethylamino-propyl)-piperazine-1-carboxylic acid benzhydryl-amide | 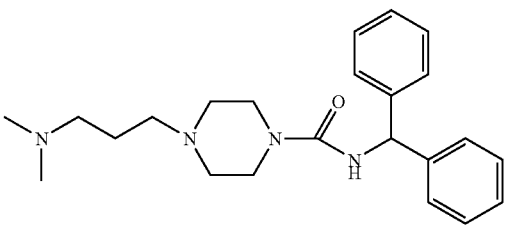 |
| 12 | 4-(1-Methyl-piperidin-3-ylmethyl)-piperazine-1-carboxylic acid benzhydryl-amide | 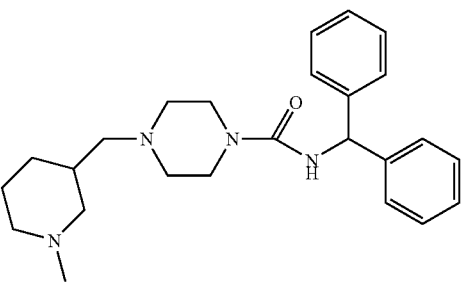 |
| 13 | 4-(Phenyl-pyridin-3-yl-methyl)-piperazine-1-carboxylic acid benzhydryl-amide | 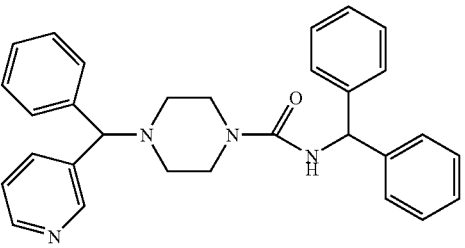 |

-continued

| Compound No. | Name | Structure |
|---|---|---|
| 14 | 4-(Phenyl-pyridin-2-yl-methyl)-piperazine-1-carboxylic acid benzhydryl-amide | 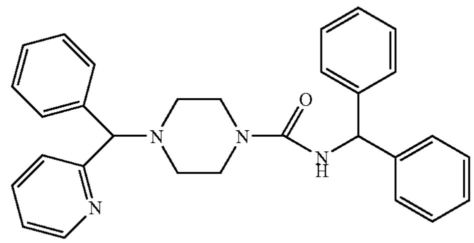 |
| 15 | 4-[(4-tert-Butyl-phenyl)-phenyl-methyl]-piperazine-1-carboxylic acid benzhydryl-amide | 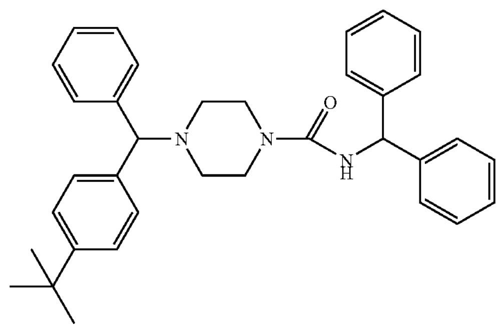 |
| 16 | 4-[(4-Methoxy-phenyl)-phenyl-methyl]-piperazine-1-carboxylic acid benzhydryl-amide | 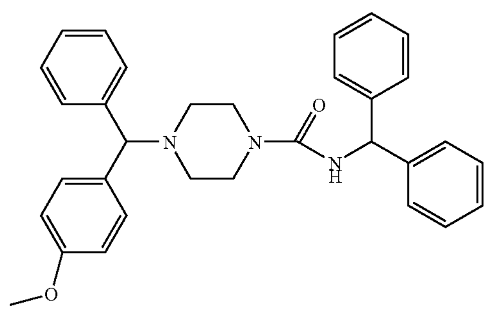 |
| 17 | 4-[(4-Benzyloxy-phenyl)-phenyl-methyl]-piperazine-1-carboxylic acid benzhydryl-amide | 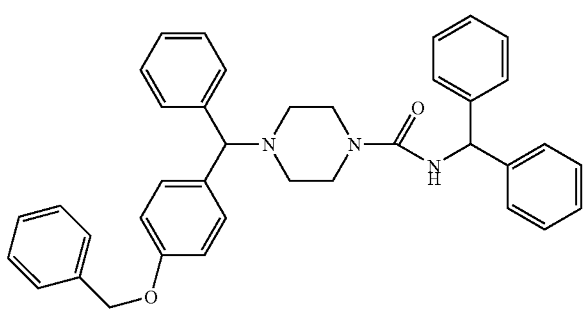 |
| 18 | 4-[(4-Hydroxy-phenyl)-phenyl-methyl]-piperazine-1-carboxylic acid benzhydryl-amide | 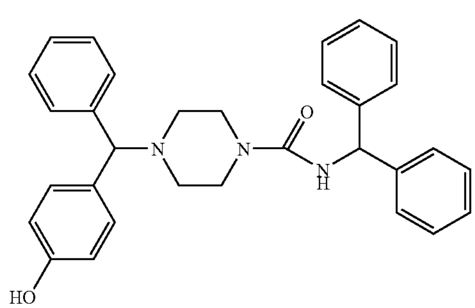 |

-continued

| Compound No. | Name | Structure |
|---|---|---|
| 19 | 4-Benzhydryl-2,5-dioxo-piperazine-1-carboxylic acid benzhydryl-amide | 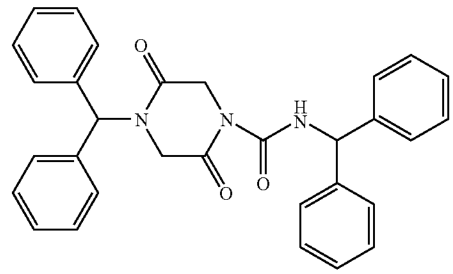 |
| 20 | 4-[(1-Methyl-piperidin-4-yl)-phenyl-methyl]-piperazine-1-carboxylic acid benzhydryl-amide | 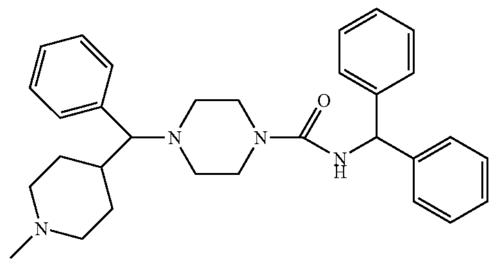 |
| 21 | 4-[(2-pyrrolidin-1-yl ethyl]-piperazine-1-carboxylic acid benzhydryl-amide | 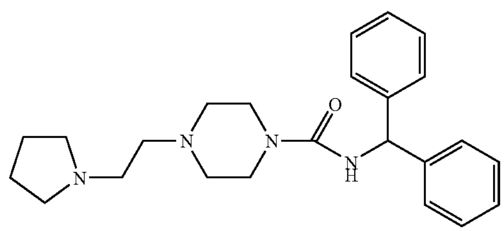 |
| 22 | 4-[(1-Methyl-piperidin-3-yl)-phenyl-methyl]-piperazine-1-carboxylic acid benzhydryl-amide | 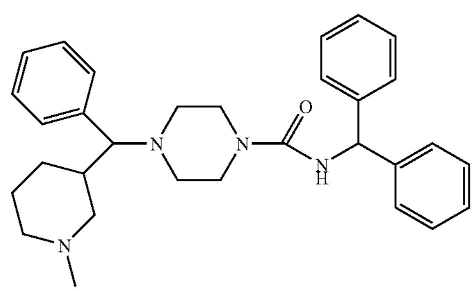 |
| 23 | 4-[(1-Methyl-piperidin-4-yl)-(4-fluoro-phenyl)-methyl]-piperazine-1-carboxylic acid benzhydryl-amide | 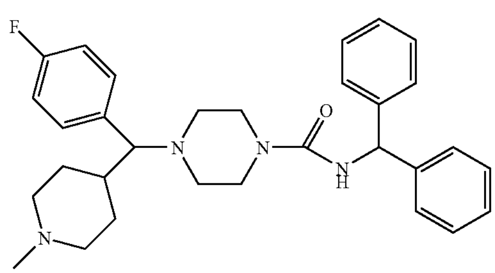 |

| Compound No. | Name | Structure |
|---|---|---|
| 24 | 4-[(1-Methyl-piperidin-4-yl)-(4-chloro-phenyl)-methyl]-piperazine-1-carboxylic acid benzhydryl-amide | 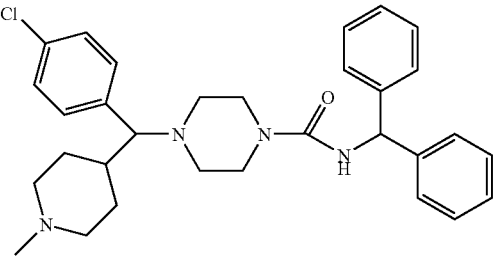 |
| 25 | 4-[(1-methyl-pyrrolidin-2-yl methyl]-piperazine-1-carboxylic acid benzhydryl-amide | 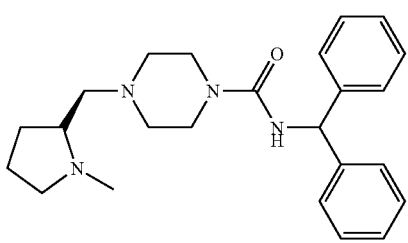 |
| 26 | 4-[(1-Phenyl-piperidin-4-yl)-methyl]-piperazine-1-carboxylic acid benzhydryl-amide | 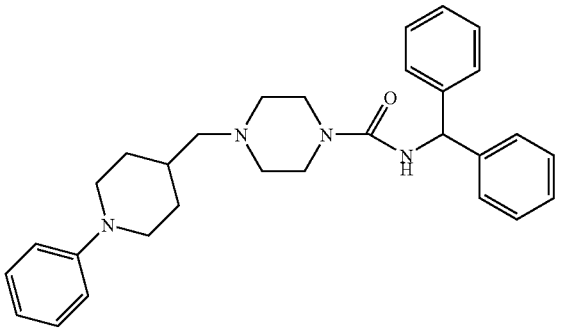 |
| 27 | 4-cyclopropylmethyl-piperazine-1-carboxylic acid benzhydryl-amide | 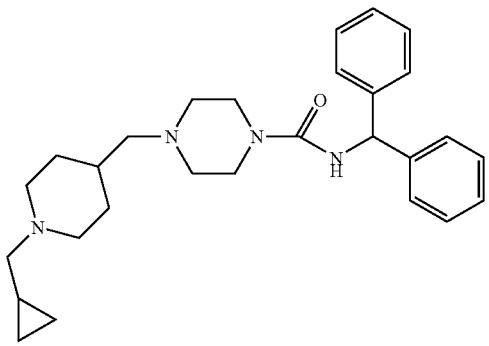 |
| 28 | 4-[(1-Benzyl-piperidin-4-yl)-methyl]-piperazine-1-carboxylic acid benzhydryl-amide | 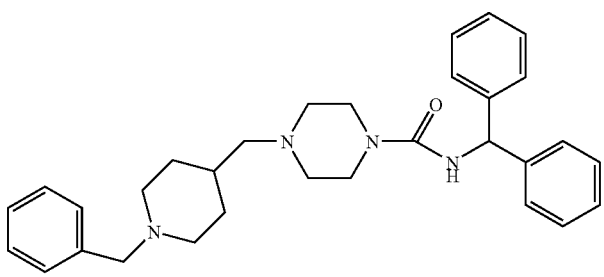 |

-continued

| Compound No. | Name | Structure |
|---|---|---|
| 29 | 4-[(1-Methyl-piperidin-2-yl)-methyl]-piperazine-1-carboxylic acid benzhydryl-amide | 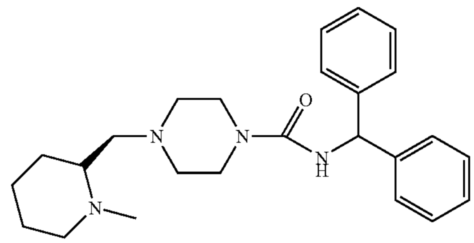 |
| 30 | 2,6-Dimethyl-4-[(1-benzyl-piperidin-4-yl)-methyl]-piperazine-1-carboxylic acid benzhydryl-amide | 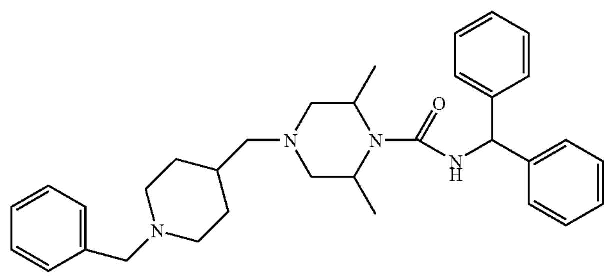 |
| 31 | 3-Methyl-4-[(1-benzyl-piperidin-4-yl)-methyl]-piperazine-1-carboxylic acid benzhydryl-amide | 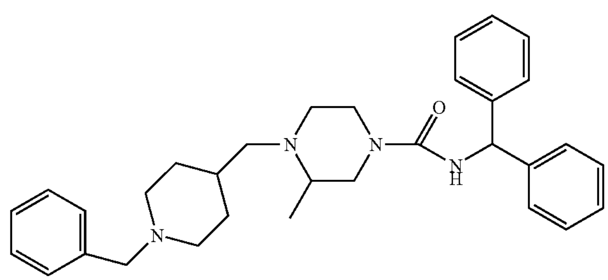 |
| 32 | 4-(2-pyrrolidin-1-yl ethyl)-piperazine-1-carboxylic acid benzhydryl-methyl-amide | 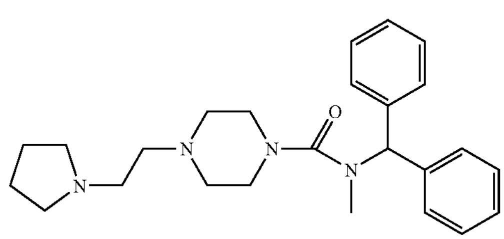 |
| 33 | 4-[(4-tert-Butyl-phenyl)-phenyl-methyl]-piperazine-1-carboxylic acid benzhydryl-methyl-amide | 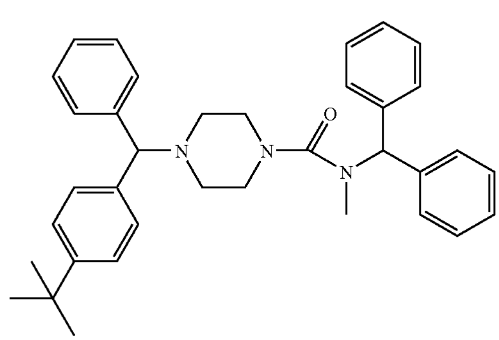 |

-continued

| Compound No. | Name | Structure |
|---|---|---|
| 34 | 4-[(1-Benzyl-piperidin-4-yl)-phenyl-methyl]-piperazine-1-carboxylic acid benzhydryl-amide | 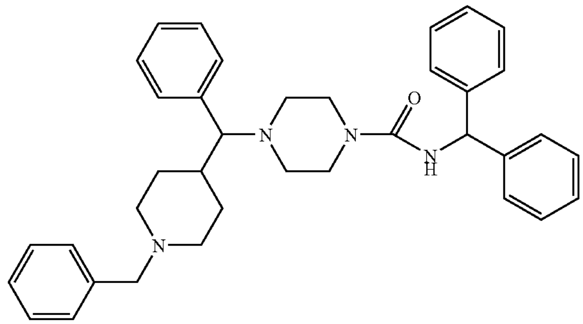 |
| 35 | 4-[Piperidin-4-yl-phenyl-methyl]-piperazine-1-carboxylic acid benzhydryl-amide | 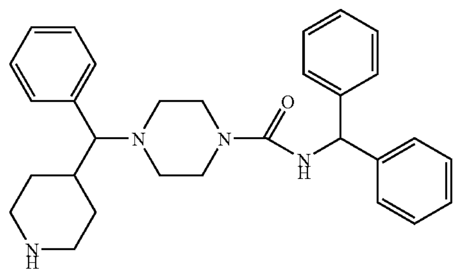 |
| 36 | 4-[(1-Methyl-piperidin-4-yl)-(2,4-dimethyl-phenyl)-methyl]-piperazine-1-carboxylic acid benzhydryl-amide | 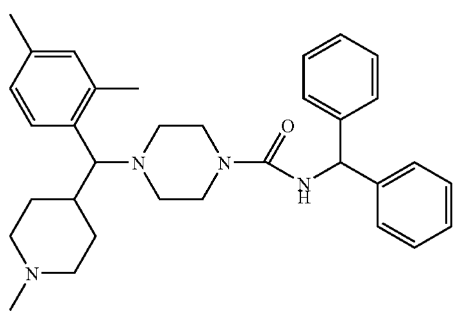 |
| 37 | 4-[(1-Methyl-piperidin-4-yl)-(2-chloro-phenyl)-methyl]-piperazine-1-carboxylic acid benzhydryl-amide | 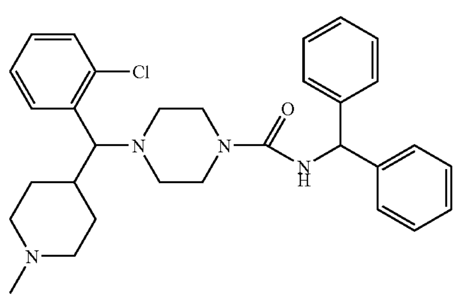 |
| 38 | 4-[(1-Methyl-piperidin-4-yl)-(3-chloro-phenyl)-methyl]-piperazine-1-carboxylic acid benzhydryl-amide | 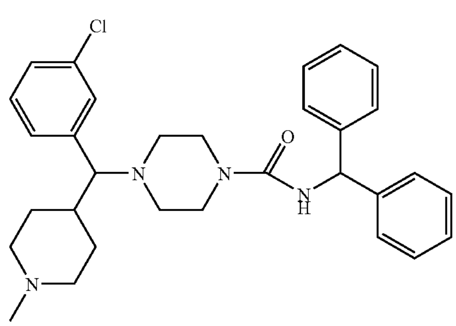 |

-continued

| Compound No. | Name | Structure |
|---|---|---|
| 39 | 4-(Diphenyl-methyl)-piperazine-1-carboxylic acid benzhydryl-methyl-amide | 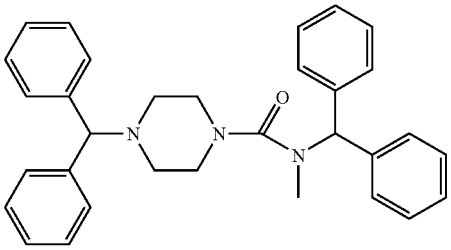 |
| 40 | 4-[(1-Methyl-4-phenyl-piperidin-4-yl)-methyl]-piperazine-1-carboxylic acid benzhydryl-amide | 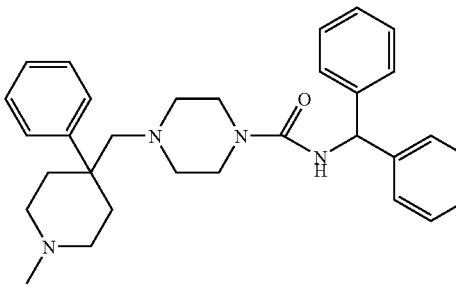 |
| 41 | 2,6-Dimethyl-4-[(1-methyl-piperidin-4-yl)-methyl]-piperazine-1-carboxylic acid benzhydryl-amide | 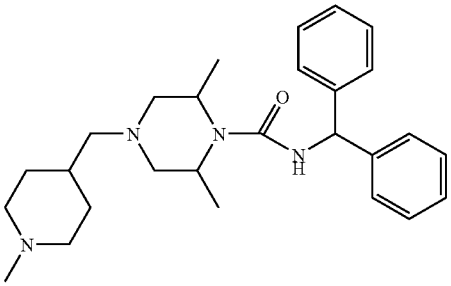 |
| 42 | N-[bis(4-methylphenyl)methyl]-2,6-dimethyl-4-[(1-methyl-piperidin-4-yl)-methyl]-piperazine-1-carboxamide | 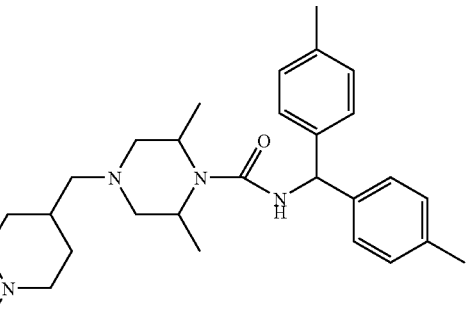 |
| 43 | N-[bis(4-fluorophenyl)methyl]-2,6-dimethyl-4-[(1-methyl-piperidin-4-yl)-methyl]-piperazine-1-carboxamide | 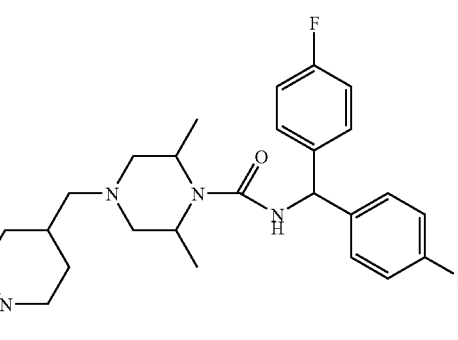 |

-continued

| Compound No. | Name | Structure |
|---|---|---|
| 44 | N-[bis(3-fluorophenyl)methyl]-2,6-dimethyl-4-[(1-methyl-piperidin-4-yl)-methyl]-piperazine-1-carboxamide | 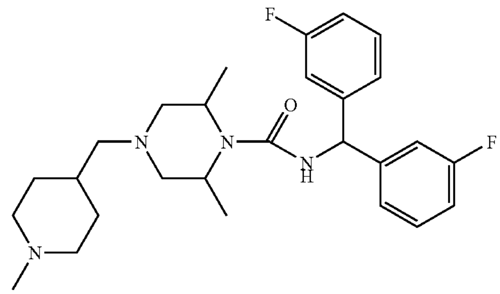 |
| 45 | N-[bis(4-chlorophenyl)methyl]-4-[(1-methyl-piperidin-4-yl)-methyl]-piperazine-1-carboxamide | 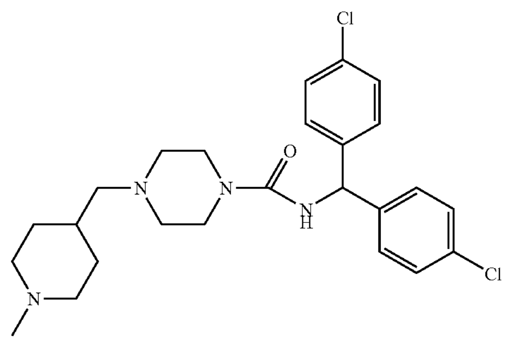 |
| 46 | N-[bis(4-methylphenyl)methyl]-4-[(1-methyl-piperidin-4-yl)-methyl]-piperazine-1-carboxamide | 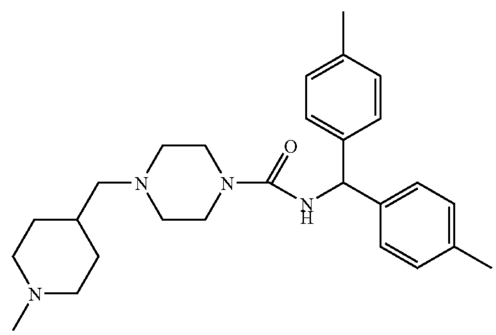 |
| 47 | N-[bis(4-fluorophenyl)methyl]-4-[(1-methyl-piperidin-4-yl)-methyl]-piperazine-1-carboxamide | 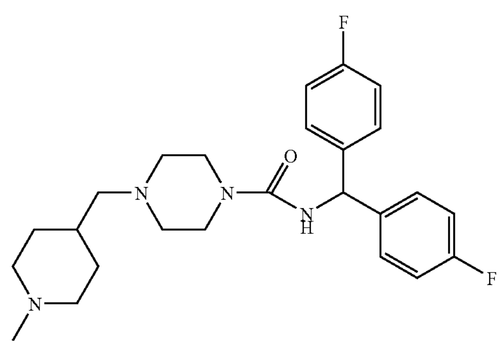 |

| Compound No. | Name | Structure |
|---|---|---|
| 48 | N-[bis(3-fluorophenyl)methyl]-4-[(1-methyl-piperidin-4-yl)-methyl]-piperazine-1-carboxamide | 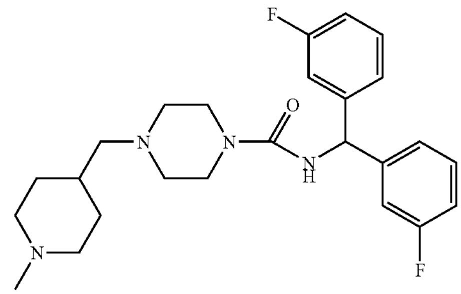 |
| 49 | 4-[Methyl-(1-methyl-piperidin-4-yl)-phenyl-methyl]-piperazine-1-carboxylic acid benzhydryl-amide | 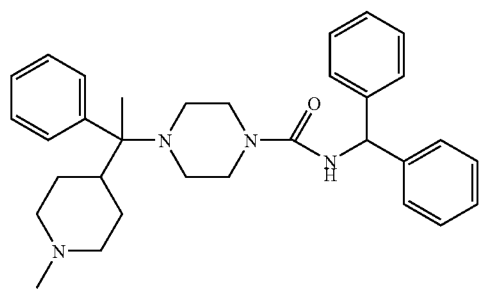 |
| 50 | N-[bis(4-methylphenyl)methyl]-4-(3-dimethylaminopropyl)-piperazine-1-carboxamide | 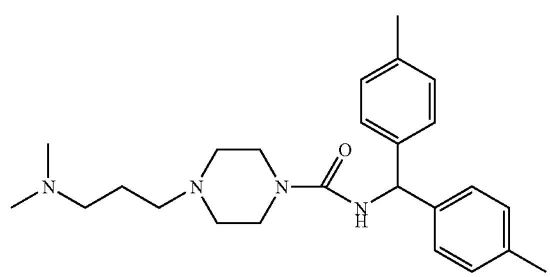 |
| 51 | N-[bis(4-fluorophenyl)methyl]-4-(3-dimethylaminopropyl)-piperazine-1-carboxamide | 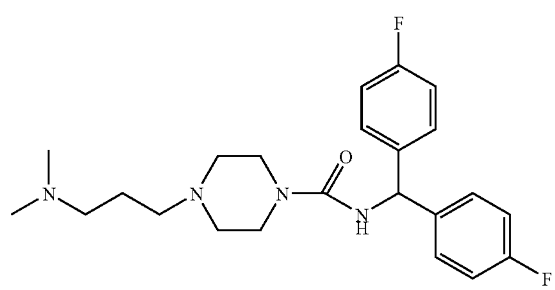 |
| 52 | N-[bis(4-chlorophenyl)methyl]-4-(3-dimethylaminopropyl)-piperazine-1-carboxamide | 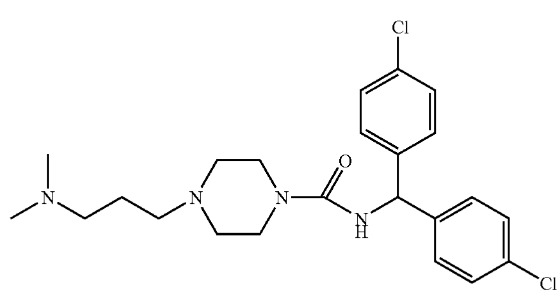 |

-continued

| Compound No. | Name | Structure |
|---|---|---|
| 53 | N-[bis(4-chlorophenyl)methyl]-4-[(3-piperidin-1-yl)propyl]-piperazine-1-carboxamide | 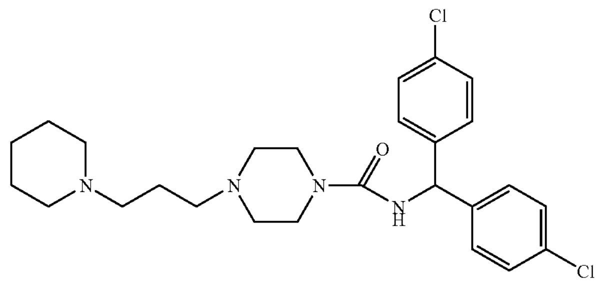 |
| 54 | N-[bis(4-fluorophenyl)methyl]-4-[(3-piperidin-1-yl)propyl]-piperazine-1-carboxamide | 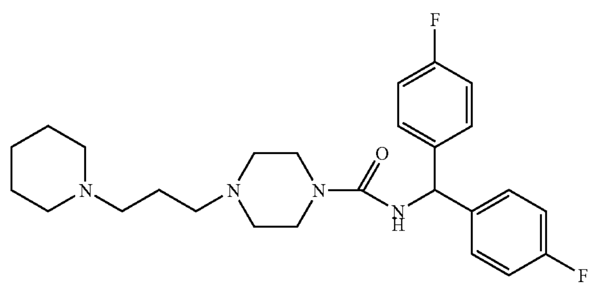 |
| 55 | N-[bis(4-methylphenyl)methyl]-4-[(3-piperidin-1-yl)propyl]-piperazine-1-carboxamide | 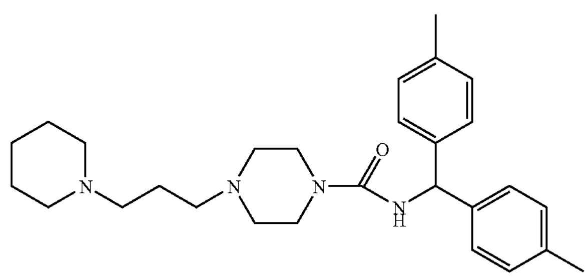 |
| 56 | N-[bis(4-methylphenyl)methyl]-4-[(3-morpholin-4-yl)propyl]-piperazine-1-carboxamide | 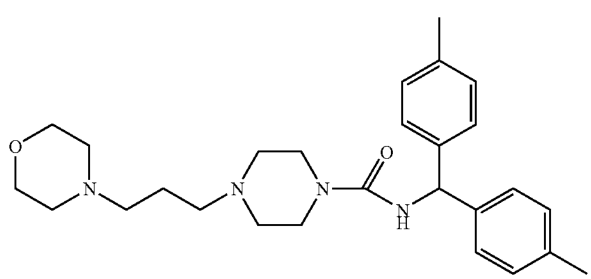 |
| 57 | N-[bis(4-fluorophenyl)methyl]-4-[(3-morpholin-4-yl)propyl]-piperazine-1-carboxamide | 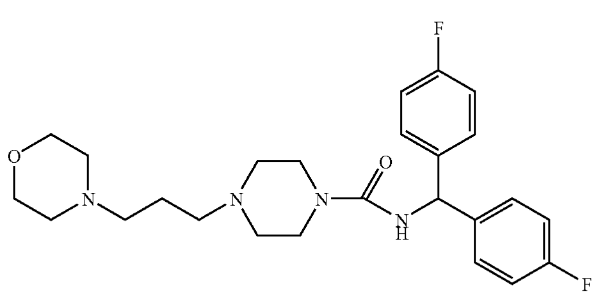 |

-continued

| Compound No. | Name | Structure |
|---|---|---|
| 58 | N-[bis(4-chlorophenyl)methyl]-4-[(3-morpholin-4-yl)propyl]-piperazine-1-carboxamide | 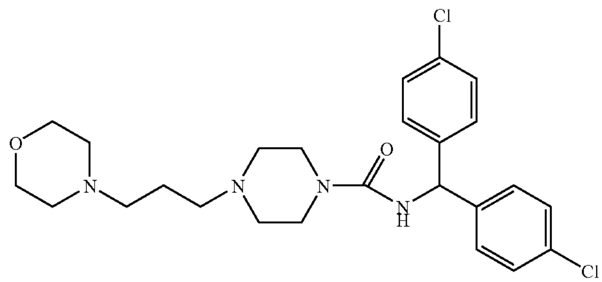 |
| 59 | N-[bis(4-chlorophenyl)methyl]-4-[(3-pyrrolidin-1-yl)propyl]-piperazine-1-carboxamide | 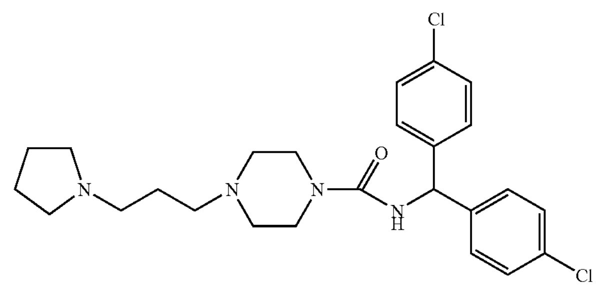 |
| 60 | N-[bis(4-fluorophenyl)methyl]-4-[(3-pyrrolidin-1-yl)propyl]-piperazine-1-carboxamide | 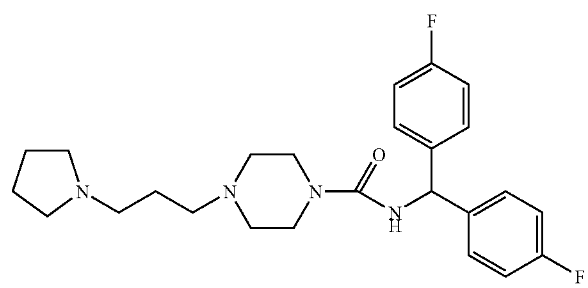 |
| 61 | N-[bis(4-methylphenyl)methyl]-4-[(3-pyrrolidin-1-yl)propyl]-piperazine-1-carboxamide | 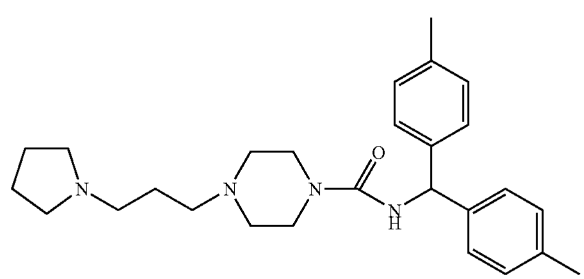 |
| 62 | N-[bis(3-fluorophenyl)methyl]-4-[(3-pyrrolidin-1-yl)propyl]-piperazine-1-carboxamide | 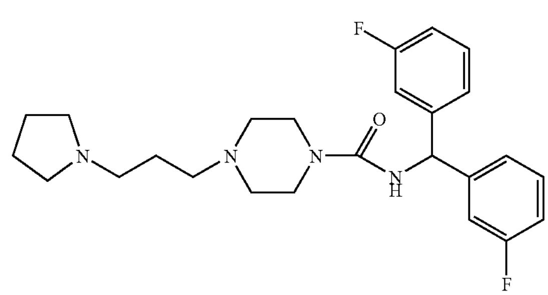 |

-continued

| Compound No. | Name | Structure |
|---|---|---|
| 63 | N-[bis(3-fluorophenyl)methyl]-4-[(3-piperidin-1-yl)propyl]-piperazine-1-carboxamide | 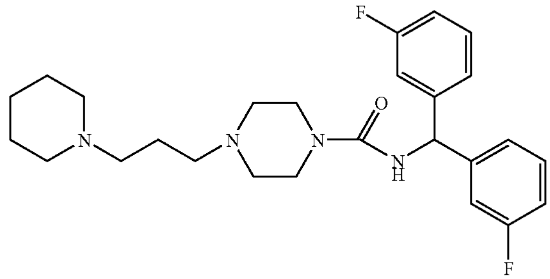 |
| 64 | N-[bis(3-fluorophenyl)methyl]-4-[(3 0morphon-4-yl)propyl]-piperazine-1-carboxamide | 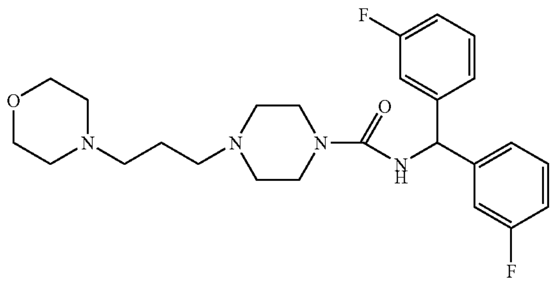 |
| 65 | N-[bis(3-fluorophenyl)methyl]-4-[(3-dimethylamino propyl]piperazine-1-carboxamide | 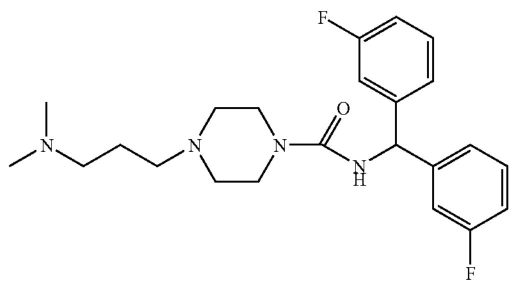 |

In a similar manner, using Reaction Scheme 1, but substituting 4-aminopiperidine for piperazine, the compounds above where Z is CHNH, rather than N are prepared.

EXAMPLE 17

N-type Channel Blocking Activities of Various Invention Compounds

A. Transformation of HEK cells

N-type calcium channel blocking activity was assayed in human embryonic kidney cells, HEK 293, stably transfected with the rat brain N-type calcium channel subunits ($\alpha_{1B}$+ $\alpha_2\delta$+$\beta_{1b}$ cDNA subunits). Alternatively, N-type calcium channels ($\alpha_{1B}$+$\alpha_2\delta$+$\beta_{1b}$ cDNA subunits), L-type channels ($\alpha_{1C}$+$\alpha_2\delta$+$\beta_{1b}$ cDNA subunits) and P/Q-type channels ($\alpha_{1A}$+ $\alpha_2\delta$+$\beta_{1b}$ cDNA subunits) were transiently expressed in HEK 293 cells. Briefly, cells were cultured in Dulbecco's modified eagle medium (DMEM) supplemented with 10% fetal bovine serum, 200 U/ml penicillin and 0.2 mg/ml streptomycin at 37° C. with 5% $CO_2$. At 85% confluency cells were split with 0.25% trypsin/1 mM EDTA and plated at 10% confluency on glass coverslips. At 12 hours the medium was replaced and the cells transiently transfected using a standard calcium phosphate protocol and the appropriate calcium channel cDNA's. Fresh DMEM was supplied and the cells transferred to 28° C./5% $CO_2$. Cells were incubated for 1 to 2 days prior to whole cell recording.

B. Measurement of Inhibition

Whole cell patch clamp experiments were performed using an Axopatch 200B amplifier (Axon Instruments, Burlingame, Calif.) linked to a personal computer equipped with pCLAMP software. The external and internal recording solutions contained, respectively, 5 mM $BaCl_2$, 10 mM $MgCl_2$, 10 mM HEPES, 40 mM TEAC1, 10 mM glucose, 87.5 mM CsCl (pH 7.2) and 108 mM CsMS, 4 mM $MgCl_2$, 9 mM EGTA, 9 mM HEPES (pH 7.2). Currents were typically elicited from a holding potential of −80 mV to +10 mV using Clampex software (Axon Instruments). Typically, currents were first elicited with low frequency stimulation (0.067 Hz) and allowed to stabilize prior to application of the compounds. The compounds were then applied during the low frequency pulse trains for two to three minutes to assess tonic block, and subsequently the pulse frequency was increased to 0.2 Hz to assess frequency dependent block. Data were analyzed using Clampfit (Axon Instruments) and SigmaPlot 4.0 (Jandel Scientific).

Specific data obtained for N-type channels are shown in Table 2 below.

TABLE 2

N-type Calcium Channel Block

| Compound | IC$_{50}$ @ 0.067 Hz (μM) | IC$_{50}$ @ 0.2 Hz (μM) |
| --- | --- | --- |
| 1 | 0.20 | 0.15 |
| 2 | 1.48 | 1.48 |
| 3 | 2.71 | 2.71 |
| 4 | 0.29 | 0.28 |
| 5 | 0.39 | 0.34 |
| 6 | 0.28 | 0.18 |
| 7 | 0.23 | 0.20 |
| 10 | 0.26 | 0.26 |
| 11 | 2.17 | 0.99 |
| 12 | 1.70 | 0.49 |
| 21 | 1.00 | 1.00 |
| 22 | 6.30 | 2.15 |
| 24 | 4.31 | 2.46 |
| 25 | >5.90 | 8.80 |
| 32 | >20 | >8.80 |
| 35 | 3.47 | 2.16 |
| 37 | 1.33 | 0.91 |
| 38 | 3.31 | 1.56 |
| 39 | 0.66 | 0.31 |

EXAMPLE 18

T-type Channel Blocking Activities of Various Invention Compounds

Standard patch-clamp techniques were employed to identify blockers of T-type currents. Briefly, previously described HEK cell lines stably expressing human DiG T-type channels were used for all the recordings (passage #: 4-20, 37° C., 5% CO$_2$). To obtain T-type currents, plastic dishes containing semi-confluent cells were positioned on the stage of a ZEISS AXIOVERT S100 microscope after replacing the culture medium with external solution (see below). Whole-cell patches were obtained using pipettes (borosilicate glass with filament, O.D.: 1.5 mm, I.D.: 0.86 mm, 10 cm length), fabricated on a SUTTER P-97 puller with resistance values of ~5 MΩ (see below for internal solution).

TABLE 3

External Solution 500 ml - pH 7.4, 265.5 mOsm

| Salt | Final mM | Stock M | Final ml |
| --- | --- | --- | --- |
| CsCl | 132 | 1 | 66 |
| CaCl$_2$ | 2 | 1 | 1 |
| MgCl$_2$ | 1 | 1 | 0.5 |
| HEPES | 10 | 0.5 | 10 |
| glucose | 10 | — | 0.9 grams |

TABLE 4

Internal Solution 50 ml - pH 7.3 with CsOH, 270 mOsm

| Salt | Final mM | Stock M | Final ml |
| --- | --- | --- | --- |
| Cs-Methanesulfonate | 108 | — | 1.231 gr/50 ml |
| MgCl2 | 2 | 1 | 0.1 |
| HEPES | 10 | 0.5 | 1 |

TABLE 4-continued

Internal Solution 50 ml - pH 7.3 with CsOH, 270 mOsm

| Salt | Final mM | Stock M | Final ml |
| --- | --- | --- | --- |
| EGTA-Cs | 11 | 0.25 | 2.2 |
| ATP | 2 | 0.2 | 0.025 |
| | | | (1 aliquot/2.5 ml) |

T-type currents were reliably obtained by using two voltage protocols:

(1) "non-inactivating", and (2) "inactivation"

In the non-inactivating protocol, the holding potential is set at −110 mV and with a pre-pulse at −100 mV for 1 second prior to the test pulse at −40 mV for 50 ms. In the inactivation protocol, the pre-pulse is at approximately −85 mV for 1 second, which inactivates about 15% of the T-type channels.

Test compounds were dissolved in external solution, 0.1-0.01% DMSO. After ~10 min rest, they were applied by gravity close to the cell using a WPI microfil tubing. The "non-inactivated" pre-pulse was used to examine the resting block of a compound. The "inactivated" protocol was employed to study voltage-dependent block. However, the initial data shown below were mainly obtained using the non-inactivated protocol only. IC$_{50}$ values are shown for various compounds of the invention in Table 5.

TABLE 5

T-type Calcium Channel Block

| Compound | IC$_{50}$ @ −100 mV (μM) | IC$_{50}$ @ −80 mV (μM) |
| --- | --- | --- |
| 1 | 0.583 | 0.231 |
| 2 | 0.221 | 0.066 |
| 3 | 0.075 | 0.028 |
| 4 | 0.171 | 0.056 |
| 5 | 0.242 | 0.053 |
| 6 | 0.147 | 0.047 |
| 7 | 4.20 | 0.324 |
| 10 | 20 | 20 |
| 20 | 5.10 | 3.40 |
| 21 | 15 | 2.00 |
| 32 | >23 | >6.72 |
| 35 | 0.663 | |
| 36 | 1.90 | 1.30 |

EXAMPLE 19

Activity of Invention Compounds in Formalin-Induced Pain Model

The effects of intrathecally delivered compounds of the invention on the rat formalin model were measured. The compounds were reconstituted to stock solutions of approximately 10 mg/ml in propylene glycol. Eight Holtzman male rats of 275-375 g size were randomly selected per test article.

The following study groups were used, with test article, vehicle control (propylene glycol) and saline delivered intraperitoneally (IP):

TABLE 6

Formalin Model Dose Groups

| Test/Control Article | Dose | Route | Rats per group |
|---|---|---|---|
| Compound | 30 mg/kg | IP | 6 |
| Propylene glycol | N/A | IP | 4 |
| Saline | N/A | IP | 7 |

N/A = Not Applicable

Prior to initiation of drug delivery baseline behavioral and testing data were taken. At selected times after infusion of the Test or Control Article these data were again collected.

On the morning of testing, a small metal band (0.5 g) was loosely placed around the right hind paw. The rat was placed in a cylindrical Plexiglas chamber for adaptation a minimum of 30 minutes. Test Article or Vehicle Control Article was administered 10 minutes prior to formalin injection (50 µl of 5% formalin) into the dorsal surface of the right hind paw of the rat. The animal was then placed into the chamber of the automated formalin apparatus where movement of the formalin injected paw was monitored and the number of paw flinches tallied by minute over the next 60 minutes (Malmberg, A. B., et al., *Anesthesiology* (1993) 79:270-281).

Results are presented as Maximum Possible Effect ±SEM, where saline control=100%.

TABLE 7

% Maximal Possible Effect in Formalin-Induced Pain Model

| Compound | Phase I (% MPE) | Phase II Total (% MPE) | Phase IIA (% MPE) | Phase IIB (% MPE) |
|---|---|---|---|---|
| 1 | 58 ± 15 | 75 ± 12 | 65 ± 12 | 99 ± 15 |
| 4 | 71 ± 15 | 74 ± 11 | 70 ± 13 | 88 ± 9 |
| 5 | 54 ± 11 | 65 ± 10 | 52 ± 10 | 105 ± 13 |
| 6 | 53 ± 10 | 71 ± 7 | 63 ± 9 | 99 ± 5 |
| 7 | 61 ± 6 | 71 ± 7 | 63 ± 9 | 85 ± 20 |
| 11 | 59 ± 13 | 60 ± 12 | 50 ± 14 | 94 ± 22 |

EXAMPLE 20

Spinal Nerve Ligation Model of Neuropathic Pain

Spinal nerve ligation (SNL) injury was induced using the procedure of Kim and Chung, (Kim, S. H., et al., *Pain* (1992) 50:355-363) in male Sprague-Dawley rats (Harlan; Indianapolis, Ind.) weighing 200 to 300 grams. Anesthesia was induced with 2% halothane in $O_2$ at 2 L/min and maintained with 0.5% halothane in $O_2$. After surgical preparation of the rats and exposure of the dorsal vertebral column from $L_4$ to $S_2$, the $L_5$ and $L_6$ spinal nerves were tightly ligated distal to the dorsal root ganglion using 4-0 silk suture. The incision was closed, and the animals were allowed to recover for 5 days. Rats that exhibited motor deficiency (such as paw-dragging) or failure to exhibit subsequent tactile allodynia were excluded from further testing. Sham control rats underwent the same operation and handling as the experimental animals, but without SNL.

The assessment of tactile allodynia consisted of measuring the withdrawal threshold of the paw ipsilateral to the site of nerve injury in response to probing with a series of calibrated von Frey filaments. Each filament was applied perpendicularly to the plantar surface of the ligated paw of rats kept in suspended wire-mesh cages. Measurements were taken before and after administration of drug or vehicle. Withdrawal threshold was determined by sequentially increasing and decreasing the stimulus strength ("up and down" method), analyzed using a Dixon non-parametric test (Chaplan, S. R., et al., *J Pharmacol Exp Ther* (1994) 269:1117-1123), and expressed as the mean withdrawal threshold.

The method of Hargreaves and colleagues (Hargreaves, K., et al., *Pain* (1988) 32:77-88) was employed to assess paw-withdrawal latency to a thermal nociceptive stimulus. Rats were allowed to acclimate within a Plexiglas enclosure on a clear glass plate maintained at 30° C. A radiant heat source (i.e., high intensity projector lamp) was activated with a timer and focused onto the plantar surface of the affected paw of nerve-injured or carrageenan-injected rats. Paw-withdrawal latency was determined by a photocell that halted both lamp and timer when the paw was withdrawn. The latency to withdrawal of the paw from the radiant heat source was determined prior to carrageenan or L5/L5 SNL, 3 hours after carrageenan or 7 days after L5/L6 SNL but before drug and after drug administration. A maximal cut-off of 40 seconds was employed to prevent tissue damage. Paw withdrawal latencies were thus determined to the nearest 0.1 second. Reversal of thermal hyperalgesia was indicated by a return of the paw withdrawal latencies to the pre-treatment baseline latencies (i.e., 21 seconds). Anti nociception was indicated by a significant ($p<0.05$) increase in paw withdrawal latency above this baseline. Data were converted to % anti hyperalgesia or % anti nociception by the formula: (100×(test latency−baseline latency)/(cut-off−baseline latency) where cut-off was 21 seconds for determining anti hyperalgesia and 40 seconds for determining anti nociception.

Compound 1 was administered orally in propylene glycol solution at a dose of 30 mg/kg. The percent activity was calculated for block of tactile allodynia, thermal hyperalgesia and analgesia.

TABLE 8

% Activity in SNL Model of Neuropathic Pain

| Time (min) | Tactile Allodynia (% Activity) | Thermal Hyperalgesia (% Activity) | Analgesia (% Activity) |
|---|---|---|---|
| 30 | 35.77 ± 10.38 | 46.98 ± 15.09 | 82.47 ± 10.11 |
| 60 | 80.89 ± 13.30 | 97.86 ± 2.14 | 88.95 ± 8.30 |
| 90 | 35.49 ± 9.01 | 49.07 ± 10.17 | 9.02 ± 5.66 |
| 120 | 19.61 ± 6.78 | 33.36 ± 10.62 | 0.00 ± 0.00 |
| 150 | 1.98 ± 1.42 | | |

Other documents of interest include:

Bourinet, E., Soong, T. W., Sutton, K., Slaymaker, S., Mathews, E., Monteil, A., Zamponi, G. W., Nargeot, J., and Snutch, T. P., "Splicing of alpha 1A subunit gene generates phenotypic variants of P- and Q-type calcium channels," *Nature Neuroscience* (1999) 2:407-415.

De Waard, M., Gurnet, C. A., and Campbell, K. T., (1996) "Structural and functional diversity of voltage activated calcium channels," in: Narahashi, T., ed., *Ion Channels*, Plenum Press, New York.

Dunlap, K., Luebke, J. I., and Turner, T. J., "Exocytotic Ca2+ channels in mammalian central neurons," *Trends Neurosci* (1995) 18:89-98.

Jones, O. T., "Ca2+ channels and epilepsy," *Eur J Pharmacol* (2002) 447:211-225.

McCleskey, E. W., and Schroeder, J. E., "Functional properties of voltage dependent calcium channels," *Cur. Topics Membr* (1991) 39:295-326.

Penn, R. D., and Paice, J. A., "Adverse effects associated with the intrathecal administration of ziconotide," *Pain* (2000) 85:291-296.

Perez-Reyes, E., "Molecular physiology of low-voltage-activated T-type calcium channels," *Physiol Rev* (2003) 83:117-161.

Santi, C. M., Cayabyab, F. S., Sutton, K. G., McRory, J. E., Mezeyova, J., Hamming, K. S., Parker, D., Stea, A., and Snutch, T. P., "Differential inhibition of T-type calcium channels by neuroleptics," *J Neurosci* (2002) 22:396-403.

Sather, W. A., Tanabe, T., Zhang, J. F., Mori, Y., Adams, M. E., and Tsien, R. W., "Distinctive biophysical and pharmacological properties of class A (BI) calcium channel alpha 1 subunits," *Neuron* (1993) 11:291-303.

Tumilowicz, J. J., Nichols, W. W., Cholon, J. J., and Greene, A. E., "Definition of a continuous human cell line derived from neuroblastoma," *Cancer Res* (1970) 30(8):2110-2118.

The invention claimed is:

1. A compound of the formula:

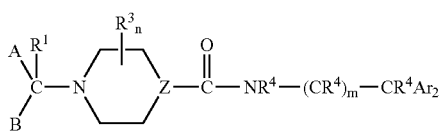

(1)

and salts thereof, wherein A is benzene;

B is piperidine;

$R^1$ is H or alkyl (1-8C), alkenyl (2-8C) or alkynyl (2-8C);

Z is N;

each $R^3$ is independently a substituent selected from the group consisting of =O, alkyl (1-8C), alkenyl (2-8C), alkynyl (2-8C), acyl, aryl, alkylaryl, halo, $CHF_2$, $CF_3$, $OCF_3$, $OCHF_2$, OCOR, CN, $NO_2$, $NR_2$, OR, SR, COR, COOR, $CONR_2$, SOR, $SO_2R$, $SO_3R$, NRCOR, NRCOOR, $OCONR_2$, SONR, $SO_2NR$, OOCR, NRSOR and $NRSO_2R$, wherein R is H or alkyl (1-8C), alkenyl (2-8C), alkynyl (2-8C), aryl, or alkylaryl, wherein two R on the same nitrogen may form a 5-7 membered ring, and wherein two substituents on adjacent carbons may form a 5-7 membered ring;

wherein each $R^4$ is independently H or alkyl (1-4C);

m is 0-3;

n is 0-2;

each Ar is phenyl; and wherein each A or B and each Ar moiety in formula (1) may be substituted by one or more substituents selected from the group consisting of =O (in nonaromatic cyclic moieties), alkyl (1-8C), alkenyl (2-8C), alkynyl (2-8C), acyl, aryl, alkylaryl, halo, $CHF_2$, $CF_3$, $OCF_3$, $OCHF_2$, OCOR, CN, $NO_2$, $NR_2$, OR, SR, COR, COOR, $CONR_2$, SOR, $SO_2R$, $SO_3R$, NRCOR, NRCOOR, $OCONR_2$, SONR, $SO_2NR$, OOCR, NRSOR and $NRSO_2R$, wherein R is H or alkyl (1-8C), alkenyl (2-8C), alkynyl (2-8C), aryl, or alkylaryl, wherein two R on the same nitrogen may form a 5-7 membered ring, and wherein two substituents on adjacent carbons may form a 5-7 membered ring, and wherein any alkyl, alkenyl, alkynyl or aryl set forth above may further be substituted by =O, alkyl (1-8C), alkenyl (2-8C), alkynyl (2-8C), acyl, aryl, alkylaryl, halo, $CHF_2$, $CF_3$, $OCF_3$, $OCHF_2$, OCOR, CN, $NO_2$, $NR_2$, OR, SR, COR, COOR, $CONR_2$, SOR, $SO_2R$, $SO_3R$, NRCOR, NROR, NRCOOR, $OCONR_2$, SONR, $SO_2NR$, OOCR, NRSOR and $NRSO_2R$, wherein R is H or alkyl (1-8C), alkenyl (2-8C), alkynyl (2-8C), aryl, or alkylaryl, wherein two R on the same nitrogen may form a 5-7 membered ring, and wherein two substituents on adjacent carbons may form a 5-7 membered.

2. The compound of claim 1, wherein $R^1$ is H.

3. The compound of claim 1, wherein n is 0.

4. The compound of claim 1, wherein m is 0.

5. The compound of claim 1, wherein n is 2 and $R^3$ is =O or COOH.

6. The compound of claim 1, wherein each $R^4$ is H.

7. The compound of claim 1, which is

4-[(1-methyl-piperidin-4-yl)-phenyl-methyl]-piperazine-1-carboxylic acid benzhydryl-amide;

4-[(1-methyl-piperidin-3-yl)-phenyl-methyl]-piperazine-1-carboxylic acid benzhydryl-amide;

4-[(1-methyl-piperidin-4-yl)-(4-fluoro-phenyl)-methyl]-piperazine-1-carboxylic acid benzhydryl-amide;

4-[(1-methyl-piperidin-4-yl)-(4-chloro-phenyl)-methyl]-piperazine-1-carboxylic acid benzhydryl-amide;

4-[(1-benzyl-piperidin-4-yl)-phenyl-methyl]-piperazine-1-carboxylic acid benzhydryl-amide;

4-[piperidin-4-yl-phenyl-methyl]-piperazine-1-carboxylic acid benzhydryl-amide;

4-[(1-methyl-piperidin-4-yl)-(2,4-dimethyl-phenyl)-methyl]-piperazine-1-carboxylic acid benzhydryl-amide;

4-[(1-methyl-piperidin-4-yl)-(2-chloro-phenyl)-methyl]-piperazine-1-carboxylic acid benzhydryl-amide;

4-[(1-methyl-piperidin-4-yl)-(3-chloro-phenyl)-methyl]-piperazine-1-carboxylic acid benzhydryl-amide;

4-(diphenyl-methyl)-piperazine-1-carboxylic acid benzhydryl-methyl-amide; or

4-[methyl-(1-methyl-piperidin-4-yl)-phenyl-methyl]-piperazine-1-carboxylic acid benzhydryl-amide, or a salt thereof.

8. The compound of claim 1 which is coupled to polyethylene glycol.

* * * * *